(12) United States Patent
Ohta et al.

(10) Patent No.: US 11,291,885 B2
(45) Date of Patent: Apr. 5, 2022

(54) SWING ANALYSIS DEVICE, SWING ANALYSIS METHOD, AND SWING ANALYSIS SYSTEM

(71) Applicant: Mizuno Corporation, Osaka (JP)

(72) Inventors: Yasuyuki Ohta, Osaka (JP); Tetsuya Kanayama, Osaka (JP); Kensuke Maenaka, Osaka (JP)

(73) Assignee: Mizuno Corporation, Osaka (JP)

( * ) Notice: Subject to any disclaimer, the term of this patent is extended or adjusted under 35 U.S.C. 154(b) by 785 days.

(21) Appl. No.: 16/092,523

(22) PCT Filed: Mar. 8, 2018

(86) PCT No.: PCT/JP2018/009041
§ 371 (c)(1),
(2) Date: Oct. 10, 2018

(87) PCT Pub. No.: WO2018/190044
PCT Pub. Date: Oct. 18, 2018

(65) Prior Publication Data
US 2021/0213327 A1 Jul. 15, 2021

(30) Foreign Application Priority Data
Apr. 14, 2017 (JP) .............................. JP2017-080592

(51) Int. Cl.
*A63B 24/00* (2006.01)
*A63B 60/46* (2015.01)
(Continued)

(52) U.S. Cl.
CPC .......... *A63B 24/0003* (2013.01); *A63B 60/46* (2015.10); *A63B 69/3605* (2020.08);
(Continued)

(58) Field of Classification Search
CPC . A63B 24/0003; A63B 60/46; A63B 69/3605; A63B 71/0622; A63B 2102/32;
(Continued)

(56) References Cited

U.S. PATENT DOCUMENTS

| 8,210,960 B1 | 7/2012 | Davenport |
| 2009/0247312 A1 * | 10/2009 | Sato .................... A63B 69/3632 473/223 |

(Continued)

FOREIGN PATENT DOCUMENTS

| EP | 3120901 A1 * | 1/2017 | ......... A63B 24/0062 |
| EP | 3120901 A1 | 1/2017 | |

(Continued)

OTHER PUBLICATIONS

Korea Written Decision on Registration dated Oct. 11, 2019.
(Continued)

*Primary Examiner* — Jeffrey S Vanderveen
(74) *Attorney, Agent, or Firm* — Troutman Pepper Hamilton Sanders LLP; James E. Schutz; Micah B. Hensley

(57) ABSTRACT

A swing analysis device for analyzing a swing of a user of a golf club accepts input of acceleration information, angular rate information, and strain information of a shaft of the golf club, detected by a sensor attached to the shaft, calculates attitude information of the golf club in a swing period, based on the acceleration information and the angular rate information, corrects the attitude information of the golf club at impact, based on the strain information of the shaft, and displays the corrected attitude information of the golf club on a display.

15 Claims, 27 Drawing Sheets

(51) Int. Cl.
  *A63B 69/36*   (2006.01)
  *A63B 71/06*   (2006.01)
  *A63B 102/32*  (2015.01)

(52) U.S. Cl.
  CPC ...... *A63B 71/0622* (2013.01); *A63B 2102/32* (2015.10); *A63B 2220/16* (2013.01); *A63B 2220/34* (2013.01); *A63B 2220/44* (2013.01); *A63B 2220/833* (2013.01); *A63B 2225/02* (2013.01)

(58) Field of Classification Search
  CPC ............ A63B 2220/16; A63B 2220/34; A63B 2220/44; A63B 2220/833; A63B 2225/02; A63B 69/36; A63B 2220/24; A63B 2220/40; A61B 5/6895; A61B 5/11; G09B 19/0038

See application file for complete search history.

(56) References Cited

U.S. PATENT DOCUMENTS

2010/0210371 A1* 8/2010 Sato ................ A63B 60/42
                                                      473/223
2014/0179454 A1   6/2014 Worobets et al.

FOREIGN PATENT DOCUMENTS

| | | |
|---|---|---|
| JP | 2010187749 A | 9/2010 |
| JP | 2012196241 A | 10/2012 |
| JP | 2014519396 A | 8/2014 |
| JP | 2014240025 A | 12/2014 |
| WO | 2012174396 A2 | 12/2012 |

OTHER PUBLICATIONS

International Search Report dated Dec. 16, 2020 issued in European Application No. 18778788.2.
International Search Report issued in counterpart International Application No. PCT/JP2018/009041 dated May 1, 2018.

* cited by examiner

FIG.15

```
                                              ┌─1250
    NAME  [        ]
    AGE [  ]  GENDER [  ]
    EMAIL    [              ]
    ADDRESS
    HEIGHT [  ] cm
    RIGHT/LEFT    ⊙ RIGHT-    ○ LEFT-
    HANDED          HANDED       HANDED
    AVERAGE  [  ]  AVERAGE NUMBER [  ] (ROUNDS/
    SCORE           OF ROUNDS          MONTH)
    FITTER NAME [      ]
```

FIG.16

| MEASUREMENT VALUE | FIRST SHOT1* | SECOND SHOT2 | THIRD SHOT3 | FOURTH SHOT4 | FIFTH SHOT5 | AVERAGE |
|---|---|---|---|---|---|---|
| HEAD SPEED (m/s) | 33 | | | | | 33 |
| SWING TEMPO | 4 | | | | | 4 |
| TOE DOWN | 3 | | | | | 3 |
| KICK ANGLE | 3 | | | | | 3 |
| RELEASE FACTOR | 3 | | | | | 3 |
| IMPACT LIE ANGLE | 59.5 | | | | | 59.5 |
| SHAFT LEAN ANGLE | −7 | | | | | −7 |
| ATTACK ANGLE | −5 | | | | | −5 |
| FACE ANGLE | 4 | | | | | 4 |
| ▸ CLEAR ALL | ▸ DELETE | ▸ DELETE | ▸ DELETE | ▸ DELETE | ▸ DELETE | |

TO WOOD SHAFT RECOMMEND — 1308
TO IRON SHAFT RECOMMEND — 1310
START MEASUREMENT — 1304
CANCEL — 1306

FIG.17

SHAFT RECOMMEND (IRON) — 1350

| | | 1352 |
|---|---|---|
| HEAD SPEED (m/s) | 22 26 30 34 38 42 46 | 33.0 |
| SWING TEMPO | 1 2 3 4 5 6 7 8 9 | 4 |
| TOE DOWN | 1 2 3 4 5 6 7 8 9 | 3 |
| KICK ANGLE | 1 2 3 4 5 6 7 8 9 | 3 |
| RELEASE FACTOR | 1 2 3 4 5 6 7 8 9 | 3 |

FITTER'S RECOMMEND — 1354 — [MATERIAL ▼] [SHAFT ▼] [HARDNESS ▼]

1356

| STEEL SHAFT | TIP | MID | BUTT |
|---|---|---|---|
| 1  SHAFT ST1 | 6 | 4 | 4 |
| 2  SHAFT ST2 | 4 | 4 | 4 |
| 3  SHAFT ST3 | 3 | 4 | 3 |
| 4  SHAFT ST4 | 3 | 4 | 3 |
| 5  SHAFT ST5 | 4 | 5 | 5 |

1358

| GRAPHITE SHAFT | TIP | MID | BUTT |
|---|---|---|---|
| 1  SHAFT G1 | 6 | 3 | 3 |
| 2  SHAFT G2 | 6 | 4 | 5 |
| 3  SHAFT G3 | 5 | 4 | 5 |
| 4  SHAFT G4 | 5 | 3 | 5 |
| 5  SHAFT G5 | 6 | 4 | 6 |

[TO TOP SCREEN] — 1360
[GO BACK] — 1362
[TO HEAD RECOMMEND] — 1364

FIG.21

| HEAD SIZE | SMALL | | LARGE |
|---|---|---|---|
| NECK TYPE | STRAIGHT | | GOOSE |
| HEAD TYPE | MUSCLE | | DEEP CAVITY |
| LIE | UP | | FLAT |

| | CHANGE ALL | ☐ No.4 | ☑ No.5 | ☑ No.6 | ☑ No.7 | ☑ No.8 | ☑ No.9 | ☑ PW |
|---|---|---|---|---|---|---|---|---|
| LENGTH | LENGTH | | 37.75 | 37.25 | 36.75 | 36.25 | 35.75 | 35.25 |
| LOFT ANGLE | LOFT ANGLE | | 25 | 28 | 32 | 36 | 41 | 46 |
| LIE ANGLE | LIE ANGLE | | 60.5 | 61 | 61.5 | 62 | 62.5 | 63 |
| FLIGHT DISTANCE | FLIGHT DISTANCE | 181 | 173 | 165 | 152 | 140 | 124 | 108 |

GO BACK    TO SELECT SHAFT

FIG.22

FITTING MEASUREMENT VALUE

| LENGTH FROM GROUND TO KNUCKLE | HEAD SPEED (m/s) | SWING TEMPO | TOE DOWN | KICK ANGLE | RELEASE FACTOR |
|---|---|---|---|---|---|
| 0.0cm | 33.0 | 4 | 3 | 3 | 3 |

| IMPACT LIE ANGLE | SHAFT LEAN ANGLE | ATTACK ANGLE | FACE ANGLE | | |
|---|---|---|---|---|---|
| 59.5 | −7 | −5 | 4 | | |

RECOMMENDED CLUB SPECS

| MODEL NAME | | | | |
|---|---|---|---|---|
| IRON A7 | | | | |
| No. | LOFT ANGLE (DEG) | LIE ANGLE (DEG) | CLUB LENGTH (INCH) | BALANCE |
| No.5 | 25.0 | 60.5 | 37.75 | D0 |
| No.6 | 28.0 | 61.0 | 37.25 | D0 |
| No.7 | 32.0 | 61.5 | 36.75 | D0 |
| No.8 | 36.0 | 62.0 | 36.25 | D0 |
| No.9 | 41.0 | 62.5 | 35.75 | D0 |
| PW | 46.0 | 63.0 | 35.25 | D0 |

| SHAFT NAME | HARDNESS |
|---|---|
| SHAFT ST2 | R |
| GRIP NAME | GRIP TAPE |
| GRIP GR1 | SINGLE |

GO BACK | SELECT UTILITY | SELECT IRON
SELECT WEDGE | DONE

FIG.24

| SELECT ALL ○ | NUMBER OF WEDGE RECOMMENDS | ○ 44-04 | | | ○ 48-08 | ○ 49-06 | ⊘ 50-07 | ○ 51-08 | ⊘ 52-09 | ○ 53-10 | | | |
|---|---|---|---|---|---|---|---|---|---|---|---|---|---|
| CHANGE ALL | | | | | | | | | 35.25 ▸ | | | | |
| LENGTH ▸ | | | | | | | | | 52 ▸ | | | | |
| LOFT ANGLE ▸ | | | | | | | | | 63 ▸ | | | | |
| LIE ANGLE ▸ | | | 114 | 111 | 108 | 105 | 103 | 100 | 97 | 95 | 92 | 90 | |
| FLIGHT DISTANCE ▸ | | | | | | | | | | | | | |
| CHANGE ALL | | ○ 54-08 | ○ 54-12 | ○ 55-09 | ○ 55-13 | ○ 56-10 | ○ 56-14 | ○ 57-11 | ○ 57-15 | ⊘ 58-08 | ○ 58-12 | | |
| LENGTH ▸ | | | | | | | | | | 35.25 ▸ | | | |
| LOFT ANGLE ▸ | | | | | | | | | | 58 ▸ | | | |
| LIE ANGLE ▸ | | | 87 | 87 | 84 | 84 | 82 | 82 | 79 | 79 | 63 ▸ | 76 | |
| FLIGHT DISTANCE ▸ | | | | | | | | | | | 76 | | |
| CHANGE ALL | | ○ 58-16 | ○ 59-09 | ○ 60-10 | ○ 61-11 | ○ 62-12 | | | | | | | |
| LENGTH ▸ | | | | | | | | | | | | | |
| LOFT ANGLE ▸ | | | | | | | | | | | | | |

TWO ▸ — 1608

THREE
TWO 1600
1606

FIG. 25

REFERENCE IRON: IRON 7

| | NUMBER | ☐ No.4 | ☑ No.5 | ☑ No.6 | ☑ No.7 | ☑ No.8 | ☑ No.9 | ☑ PW |
|---|---|---|---|---|---|---|---|---|
| LENGTH | [LENGTH ▾] | 38.25 ▾ | 37.75 ▾ | 37.25 ▾ | 36.75 ▾ | 36.25 ▾ | 35.75 ▾ | 35.25 ▾ |
| LOFT ANGLE | [LOFT ANGLE ▾] | 22 ▾ | 25 ▾ | 28 ▾ | 32 ▾ | 36 ▾ | 41 ▾ | 46 ▾ |
| LIE ANGLE | [LIE ANGLE ▾] | 60 ▾ | 60.5 ▾ | 61 ▾ | 61.5 ▾ | 62 ▾ | 62.5 ▾ | 63 ▾ |
| FLIGHT DISTANCE | [FLIGHT DISTANCE ▾] | 181 | 173 | 165 | 152 | 140 | 124 | 108 |

| | CHANGE ALL | ☑ 3U | ☑ 4U | ☑ 5U |
|---|---|---|---|---|
| LENGTH | [LENGTH ▾] | 39.75 ▾ | 39.25 ▾ | 38.75 ▾ |
| LOFT ANGLE | [LOFT ANGLE ▾] | 19 ▾ | 22 ▾ | 25 ▾ |
| LIE ANGLE | [LIE ANGLE ▾] | 58.5 ▾ | 59 ▾ | 59.5 ▾ |
| FLIGHT DISTANCE | [FLIGHT DISTANCE ▾] | 194 | 187 | 179 |

LIE | UP | FLAT

[GO BACK] [TO SELECT SHAFT]

SWING ANALYSIS DEVICE, SWING ANALYSIS METHOD, AND SWING ANALYSIS SYSTEM

This application is a U.S. National Stage of International Patent Application No. PCT/JP2018/009041, filed 8 Mar. 2018, which claims the benefit of Japanese Application No. JP2017-080592, filed 14 Apr. 2017. The entire contents of which are hereby incorporated in their entireties by reference herein.

TECHNICAL FIELD

The present disclosure relates to techniques for analyzing a swing of a golf club.

BACKGROUND ART

In golf, it is believed that competitiveness can be enhanced by improving the rhythm and the form of a swing motion. Techniques have been known that analyze a swing of a subject using output data from a sensor attached to a golf club and present the result of analysis.

For example, Japanese Patent Laying-Open No. 2014-240025 (PTL 1) discloses a swing analysis device. The swing analysis system computes swing feature information based on output data from a motion sensor corresponding to a swing of a sporting instrument and sorts the swing feature information. The swing analysis system computes reference swing feature information to be used as a reference, based on the sorted swing feature information, and stores the computed information into a storage.

CITATION LIST

Patent Literature

PTL 1: Japanese Patent Laying-Open No. 2014-240025

SUMMARY OF INVENTION

Technical Problem

PTL 1 discloses a configuration that calculates swing feature information such as a swing orbit and a head speed using data from an acceleration sensor and an angular rate sensor. In golf, the difference in inclination of the head of the golf club or the angle of the striking face at impact makes a significant difference to the result of play. The technique according to PTL 1 is thought to have room for improvement in terms of improving accuracy of swing analysis because it does not provide detailed analysis of a swing at impact.

An object in an aspect of the present disclosure is to provide a swing analysis device, a swing analysis method, and a swing analysis system capable of accurately analyzing a swing of a golf club.

Solution to Problem

According to an embodiment, a swing analysis device for analyzing a swing of a user of a golf club is provided. The swing analysis device includes: an information input unit configured to accept input of acceleration information, angular rate information, and strain information of a shaft of the golf club, detected by a sensor attached to the shaft; an attitude calculating unit configured to calculate attitude information of the golf club in a swing period, based on the acceleration information and the angular rate information; a correction unit configured to correct attitude information of the golf club at impact, based on the strain information of the shaft; and a display control unit configured to display the attitude information of the golf club corrected by the correction unit on a display.

Preferably, the attitude information includes a lie angle indicating an angle of the shaft of the golf club relative to ground. The strain information includes a strain amount in a toe down direction of the shaft. The correction unit corrects a lie angle at the impact calculated by the attitude calculating unit, based on a strain amount in the toe down direction at the impact.

Preferably, the correction unit corrects the calculated lie angle at the impact using a first regression equation obtained by performing regression analysis where the strain amount in the toe down direction at the impact and the calculated lie angle at the impact are explanatory variables and an actually measured value of a lie angle at the impact is an object variable.

Preferably, the attitude information further includes a shaft lean angle indicating an angle of the shaft relative to a virtual plane normal to ground. The strain information further includes a strain amount in a hit ball direction of the shaft. The correction unit corrects a shaft lean angle at the impact calculated by the attitude calculating unit, based on a strain amount in the hit ball direction at the impact.

Preferably, the correction unit corrects the calculated shaft lean angle at the impact, using a second regression equation obtained by performing regression analysis where the strain amount in the hit ball direction at the impact and the calculated shaft lean angle at the impact are explanatory variables and an actually measured value of a shaft lean angle at the impact is an object variable.

Preferably, the swing analysis device further includes a standstill period calculating unit configured to calculate a first time when a combined angular rate based on the angular rate information reaches a reference threshold and calculate a period from a second time prior to the first time by a first amount of time to a third time prior to the first time by a second amount of time, as a standstill period during which the user stays still. The attitude calculating unit calculates attitude information at address of the user immediately before start of the swing period, based on the acceleration information in the standstill period.

Preferably, the swing analysis device further includes an information storage unit configured to store a difference between a predetermined angle and a lie angle calculated by the attitude calculating unit when the lie angle of the golf club is set to the predetermined angle in a state in which the shaft of the golf club is fixed by a jig placed on a plane parallel to ground, as a calibration value of the lie angle, and store a shaft lean angle calculated by the attitude calculating unit when the lie angle is set to the predetermined angle, as a calibration value of the shaft lean angle.

Preferably, the swing analysis device further includes a display control unit configured to display a presentation screen on a display to present a golf club suitable for the user from among a plurality of golf clubs prepared in advance. For each of the golf clubs prepared in advance, the display control unit displays first information based on a first index value serving as an index of flight characteristics in a right and left direction of a hit ball in the golf club and a second index value serving as an index of flight characteristics in an up and down direction of a hit ball in the golf club, on the presentation screen. The attitude information further includes an attack angle indicating an angle of a direction of a swing trajectory relative to ground at impact and a relative face angle obtained by subtracting an angle of approach from a face angle, the face angle indicating an angle of a face plane of the golf club relative to a virtual plane orthogonal to a target line direction, the angle of approach indicating an angle formed with the target line direction relative to a direction of the swing trajectory. The swing analysis device further includes a recommended value calculating unit configured to calculate a first index value recommended for the user based on a first parameter including the relative face angle and calculate a second index value recommended for the user based on a second parameter including the attack angle. The display control unit further displays second information based on the first index value recommended for the user and the second index value recommended for the user, calculated by the recommended value calculating unit, on the presentation screen.

Preferably, the display control unit further displays third information indicating the attack angle and the relative face angle calculated by the attitude calculating unit, on the presentation screen.

Preferably, the swing analysis device further includes a head speed calculating unit configured to calculate a head speed of the golf club in a swing period, based on the acceleration information and the angular rate information. The first parameter and the second parameter further include a head speed at impact.

Preferably, when the user swings the golf club multiple times, the head speed calculating unit further calculates a standard deviation of the head speed at impact multiple times. The first parameter and the second parameter further include the standard deviation.

Preferably, the display control unit displays a screen including a predicted flight distance of the golf club and a predicted flight distance of a golf club of a number different from the number of the golf club, on the display.

Preferably, the display control unit further displays a predicted flight distance of another golf club of a type different from the type of the golf club. The type includes at least two of iron type, wedge type, and utility type.

According to another embodiment, a swing analysis method for analyzing a swing of a user of a golf club is provided. The swing analysis method includes the steps of: accepting input of acceleration information, angular rate information and strain information of a shaft of the golf club, detected by a sensor attached to the shaft; calculating attitude information of the golf club in a swing period, based on the acceleration information and the angular rate information; correcting attitude information of the golf club at impact, based on the strain information of the shaft; and displaying the corrected attitude information of the golf club.

According to yet another embodiment, a swing analysis system for analyzing a swing of a user of a golf club is provided. The swing analysis system includes a sensor device attached to a shaft of the golf club, and a swing analysis device for analyzing a swing of the user based on information detected by the sensor device. The swing analysis device includes an information input unit configured to accept input of acceleration information, angular rate information, and strain information of the shaft, detected by the sensor device, an attitude calculating unit configured to calculate attitude information of the golf club in a swing period, based on the acceleration information and the angular rate information, a correction unit configured to correct attitude information of the golf club at impact, based on the strain information of the shaft, and a display control unit configured to display the attitude information of the golf club corrected by the correction unit on a display.

Advantageous Effects of Invention

According to the present disclosure, a swing of a golf club can be analyzed accurately.

BRIEF DESCRIPTION OF DRAWINGS

FIG. 15 is a diagram showing an example of an input screen for various information.

FIG. 16 is a diagram showing an example of a measurement screen.

FIG. 17 is a diagram showing an example of an iron shaft recommend screen.

FIG. 21 is a diagram showing an example of an iron head select screen.

FIG. 22 is a diagram showing an example of a confirmation screen for the selected iron.

FIG. 24 is a diagram showing another example of the wedge head select screen.

FIG. 25 is a diagram showing an example of a utility head select screen.

DESCRIPTION OF EMBODIMENTS

Embodiments of the present invention will be described below. The same or corresponding parts are denoted by the same reference signs and a description thereof may not be repeated.

In the embodiments described below, the scope of the present invention is not necessarily limited to the number, quantity, etc. mentioned in the description, unless otherwise specified. In the following embodiments, each individual component is not necessarily essential to the present invention, unless otherwise specified.

<System Configuration>

(Overall Configuration)

Figure 1:
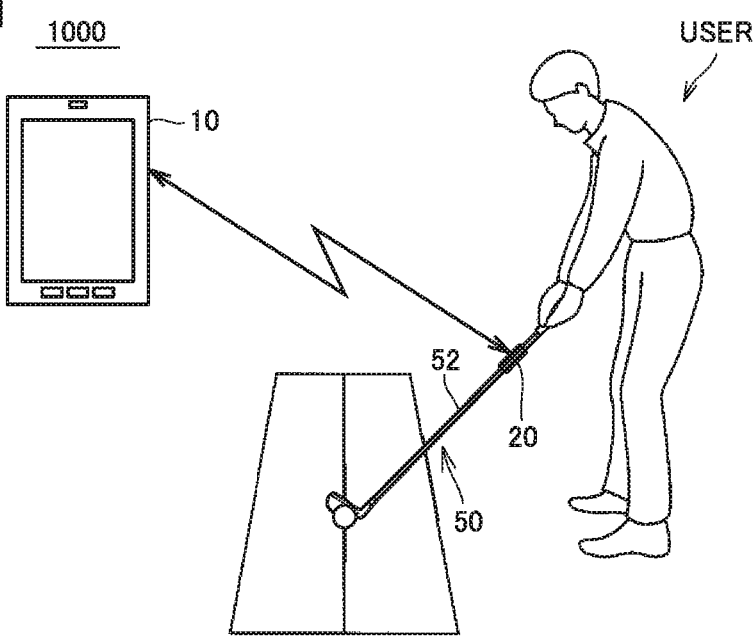
FIG. 1 is a diagram illustrating an overall configuration of a swing analysis system.

FIG. 1 is a diagram illustrating an overall configuration of a swing analysis system. Referring to FIG. 1, swing analysis system 1000 analyzes a swing of the user of a golf club and presents the analysis result to the user. Swing analysis system 1000 presents information indicating a golf club suitable for the user, based on the analysis result. Specifically, swing analysis system 1000 includes a swing analysis device 10 and a sensor device 20.

Golf club 50 includes a shaft 52, a head provided on one end of shaft 52, and a grip provided on the other end of shaft 52. Golf club 50 may be any golf club prepared by the user or prepared by others.

Swing analysis device 10 is configured with a smartphone. However, swing analysis device 10 may be implemented as a device of any kind. For example, swing analysis device 10 may be a device such as a notebook PC (personal Computer), a tablet terminal, a PDA (Personal Digital Assistance), or a desktop PC.

Swing analysis device 10 communicates with sensor device 20 using wireless communication such as Bluetooth (registered trademark), wireless LAN (Local Area Network), and infrared communication. Swing analysis device 10 may be configured to communicate with sensor device 20 using wired communication such as USB (Universal Serial Bus).

Sensor device 20 is mounted on shaft 52 such that the center of gravity of sensor device 20 is positioned, for example, about 12 inches to 15 inches from the upper end portion of the grip. Golf club 50 achieves the weight balance, for example, 14 inches from the end portion of the grip, and attaching a weight or the like at this portion does not have a significant influence on the weight balance of the entire golf club 50. Therefore, sensor device 20 is mounted at this position so that a significant change in characteristics of golf club 50 can be suppressed before and after sensor device 20 is attached.

Sensor device 20 includes an acceleration sensor, an angular rate sensor, and a strain sensor. Sensor device 20 transmits sensor data detected by each sensor, the computation result based on sensor data, and the like to swing analysis device 10. Swing analysis device 10 receives various information from sensor device 20 and performs various processing such as analysis of a swing of a subject.

(Hardware Configuration)

Figure 2:
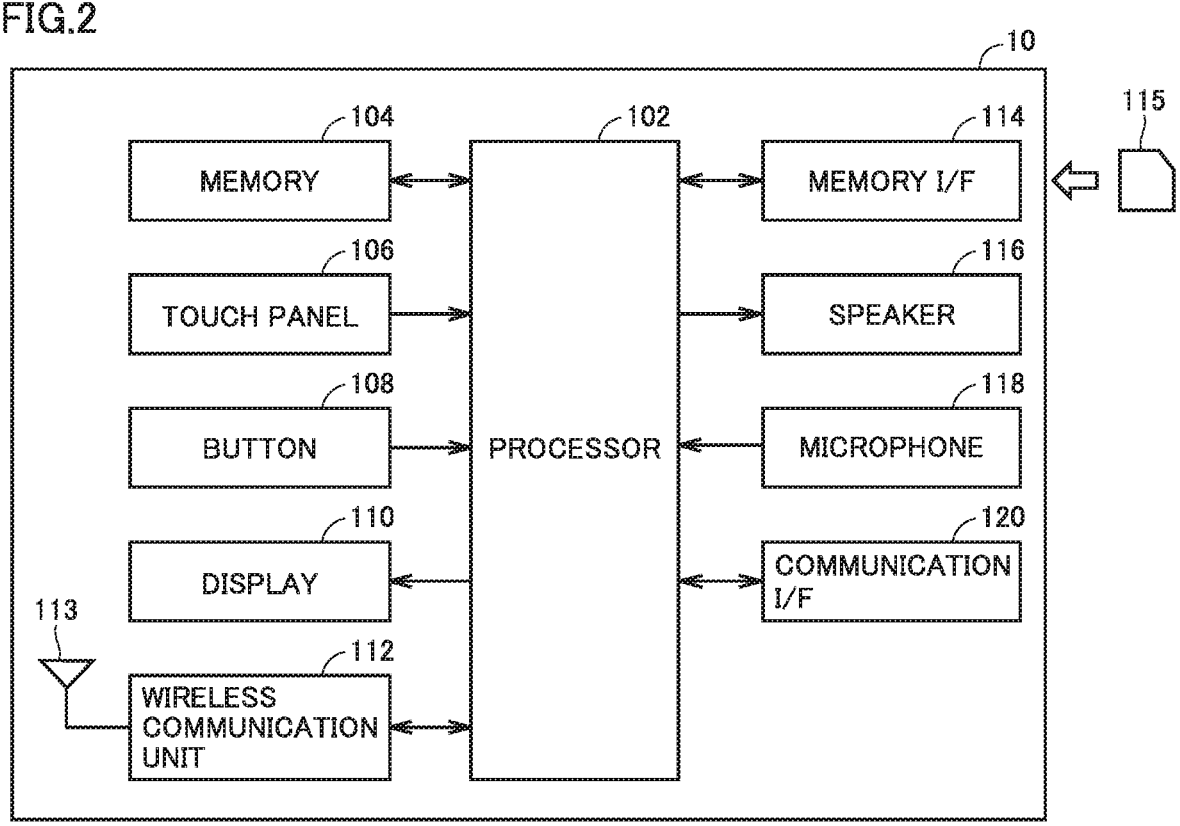
FIG. 2 is a block diagram showing a hardware configuration of a swing analysis device.

FIG. 2 is a block diagram showing a hardware configuration of the swing analysis device. Referring to FIG. 2, swing analysis device 10 includes, as main components, a processor 102, a memory 104, a touch panel 106, a button 108, a display 110, a wireless communication unit 112, a communication antenna 113, a memory interface (I/F) 114, a speaker 116, a microphone 118, and a communication interface (I/F) 120. A storage medium 115 is an external storage medium.

Processor 102 is typically an arithmetic processing unit such as a CPU (Central Processing Unit) and an MPU (Multi Processing Unit). Processor 102 reads and executes a program stored in memory 104 to control the operation of each unit in swing analysis device 10. More specifically, processor 102 executes the program to implement each of the processes (steps) of swing analysis device 10 as will be described later.

Memory 104 is implemented by a RAM (Random Access Memory), a ROM (Read-Only Memory), a flash memory, or the like. Memory 104 stores a program executed by processor 102 or data used by processor 102.

Touch panel 106 is provided on display 110 having the function serving as a display unit and may be of any type, for example, resistive or capacitive. Button 108 is disposed on a surface of swing analysis device 10 and accepts an instruction from the user to input the instruction to processor 102.

Wireless communication unit 112 connects to a mobile communication network through communication antenna 113 to transmit/receive a signal for wireless communication. Thus, swing analysis device 10 can communicate with a prescribed external device through, for example, a mobile communication network such as LTE (Long Term Evolution).

Memory interface (I/F) 114 reads data from external storage medium 115. That is, processor 102 reads data stored in external storage medium 115 through memory interface 114 and stores the data into memory 104. Processor 102 reads data from memory 104 and stores the data into external storage medium 115 through memory interface 114.

Examples of storage medium 115 include media storing a program in a nonvolatile manner, such as CD (Compact Disc), DVD (Digital Versatile Disk), BD (Blu-ray (registered trademark) Disc), USB (Universal Serial Bus) memory, memory card, FD (Flexible Disk), and hard disk.

Speaker 116 outputs sound based on an instruction from processor 102. Microphone 118 accepts voice directed to swing analysis device 10.

Communication interface (I/F) 120 is, for example, a communication interface for transmitting/receiving data between swing analysis device 10 and sensor device 20 and is implemented by an adaptor, a connector, or the like. The communication scheme is, for example, wireless communication such as Bluetooth (registered trademark) and wireless LAN or wired communication using a USB.

Figure 3:
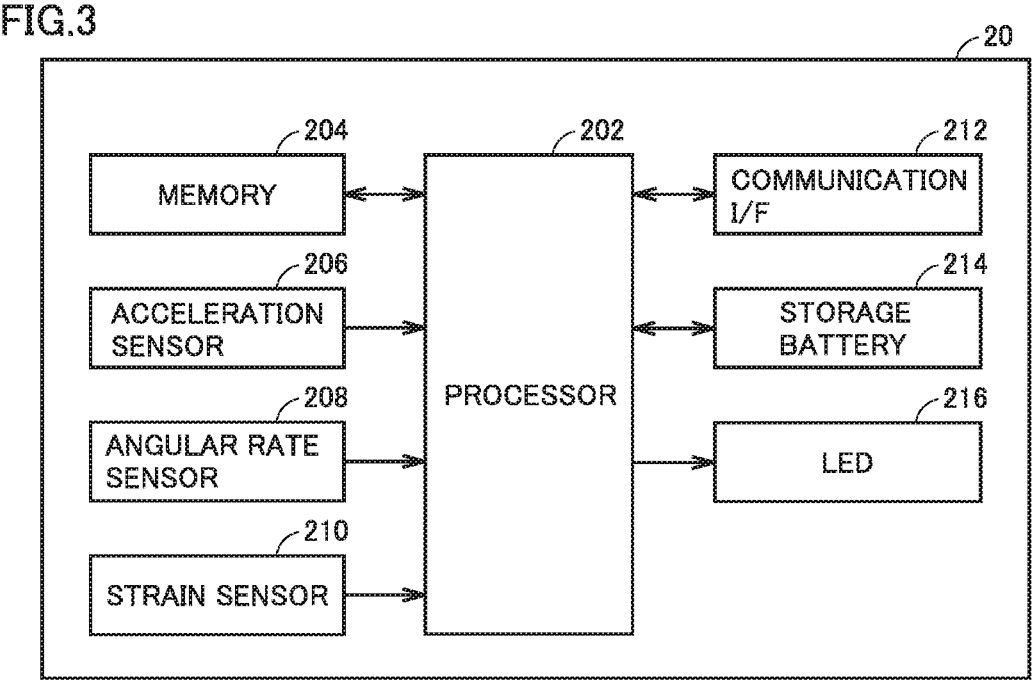
FIG. 3 is a block diagram showing a hardware configuration of a sensor device.

FIG. 3 is a block diagram showing a hardware configuration of sensor device 20. Referring to FIG. 3, sensor device 20 includes, as main components, a processor 202 for executing various processing, a memory 204 for storing a program executed by processor 202, data, and the like, an acceleration sensor 206, an angular rate sensor 208, a strain sensor 210, a communication interface (I/F) 212 for communicating with swing analysis device 10, a storage battery 214 for supplying electric power to various components in sensor device 20, and an LED (light emitting diode) 216.

Acceleration sensor 206 detects acceleration in three axis directions orthogonal to each other (hereinafter also referred to as "acceleration information"). Angular rate sensor 208 detects angular rates about three axes orthogonal to each other (hereinafter also referred to as "angular rate information").

Figure 4:
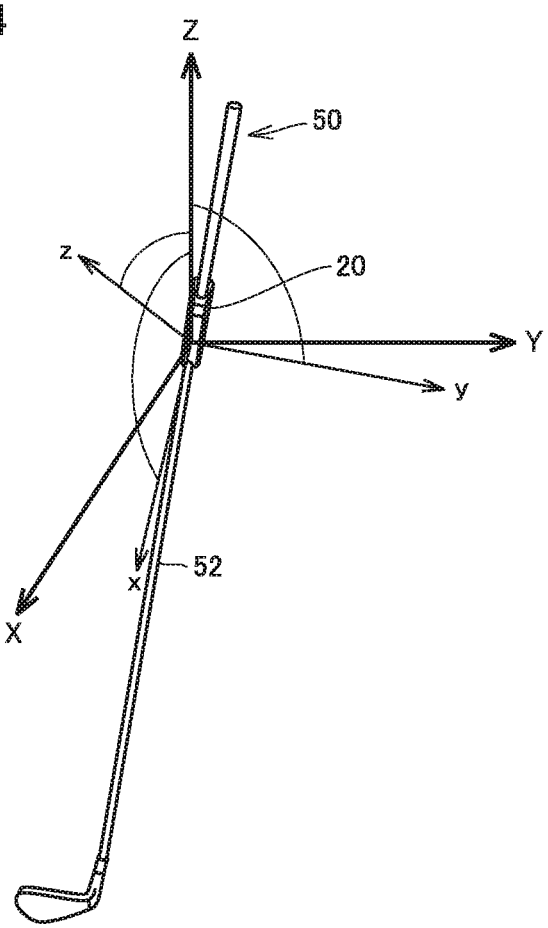
FIG. 4 is a diagram illustrating a local coordinate system and a global coordinate system.

FIG. 4 is a diagram for explaining a local coordinate system and a global coordinate system. Referring to FIG. 4, the x axis in the sensor coordinate system (local coordinate system) is set in the longitudinal direction of shaft 52, and the y axis and the z axis are each set as desired. The Z axis in the absolute coordinate system (global coordinate system) is set in the vertical direction, the Y axis is set in the user's swing direction, and the X axis is set in the normal direction to the Y axis and the Z axis.

Strain sensor 210 detects the strain amounts in the hit ball direction and the toe down direction of shaft 52 (hereinafter also referred to as "strain information"). Specifically, strain sensor 210 includes two strain gauge (strain gauge for hit ball direction) and strain gauge (strain gauge for toe down) mounted on shaft 52.

Figure 5:
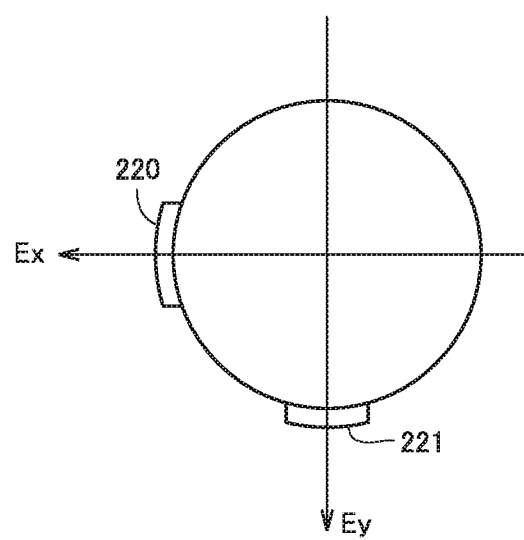
FIG. 5 is a plan view schematically showing an arrangement state of strain gauges.

FIG. 5 is a plan view schematically showing the arrangement state of the strain gauges. Specifically, FIG. 5 shows a plan view as viewed two-dimensionally from the axial direction of shaft 202 and schematically shows the arrangement state of strain gauge 220 and strain gauge 221. Referring to FIG. 5, strain gauge 220 is disposed at a portion normal to the hit ball direction (Ex direction) on the circumferential surface of shaft 52, and strain gauge 221 is affixed to a portion vertical to the direction (Ey direction) orthogonal to this hit ball direction.

Strain gauge 220 and strain gauge 221 are provided, for example, at a position about 12 inches to 15 inches from the grip-side end portion, specifically provided at a position about 14 inches from the grip-side end portion. Strain gauge 220 and strain gauge 221 are provided 90 degrees apart from each other in the circumferential direction of shaft 52.

Figure 6:
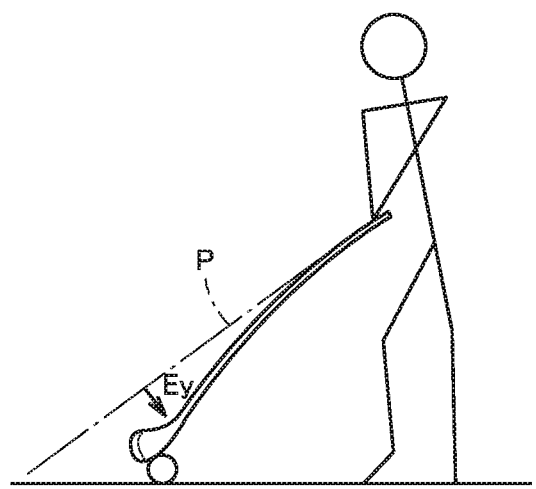
FIG. 6 is a schematic diagram showing a golfer immediately before hitting a ball, as viewed from the hit ball direction.
Figure 7:
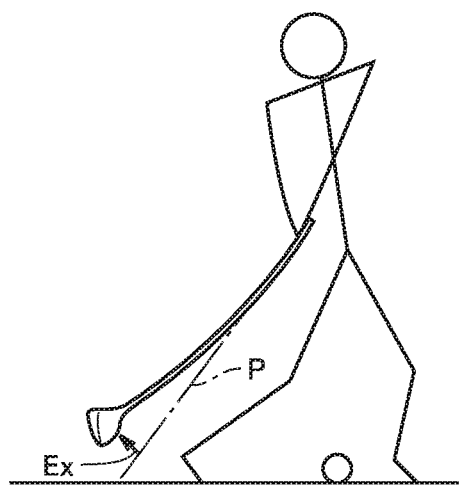
FIG. 7 is a schematic diagram showing a golfer immediately before hitting a ball, as viewed from one side.

FIG. 6 is a schematic diagram showing a golfer immediately before hitting a ball, as viewed from the hit ball direction. FIG. 7 is a schematic diagram showing a golfer immediately before hitting a ball, as viewed from one side. Referring to FIG. 6, during a swing of golf club 50, when golf club 50 swings down, the tip end of shaft 52 and the head come down from the center axis line P of shaft 52 toward the ground due the centrifugal force. This downward direction (Ey direction) is referred to as "toe down direction". Strain gauge 221 measures the strain in the Ey direction (toe down direction) of the position of shaft 52 where strain gauge 221 is mounted. Referring to FIG. 5 and FIG. 7, strain gauge 220 measures the strain in the Ex direction (hit ball direction) at a position of shaft 52 where strain gauge 220 is mounted.

<Operation Overview of System>

Figure 8:
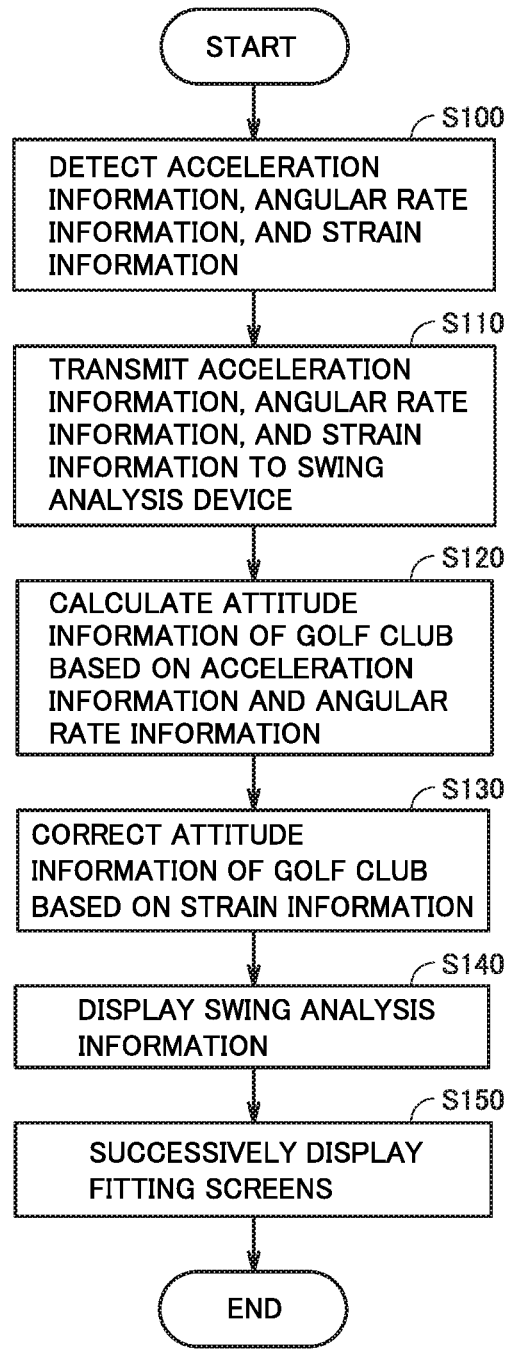
FIG. 8 is a flowchart illustrating an operation overview of the swing analysis system.

FIG. 8 is a flowchart illustrating the operation overview of swing analysis system 1000. Here, as shown in FIG. 1, it is assumed that the user hits a ball on the ground with golf club 50. Golf club 50 swung by the user is, for example, a 7-iron. Golf club 50 may be another number, such as 6-iron, or may be a wood. It is assumed that swing analysis device 10 and sensor device 20 can communicate with each other.

Referring to FIG. 8, sensor device 20 mounted on shaft 52 of golf club 50 detects acceleration information, angular rate information, and strain information in time series (step S100). Specifically, sensor device 20 detects acceleration information and angular rate information as well as strain information in the sensor coordinate system (local coordinate system) at sampling intervals (for example, 1 ms). Sensor device 20 transmits the detected acceleration information, angular rate information and strain information to swing analysis device 10 (step S110).

Swing analysis device 10 calculates head speed and attitude information of golf club 50 in a swing period, based on the acceleration information and angular rate information obtained from sensor device 20 (step S120). Specifically, swing analysis device 10 calculates the attitude angle of the head of golf club 50 at impact (that is, when the ball is hit). The attitude angle includes lie angle, attack angle, shaft lean angle, and face angle (more specifically, relative face angle as described later) at impact. In the description of the subject application, "at impact" means the same time as impact or the point of time a predetermined time (for example, about 1/1000 second) before the impact time.

Figure 9:
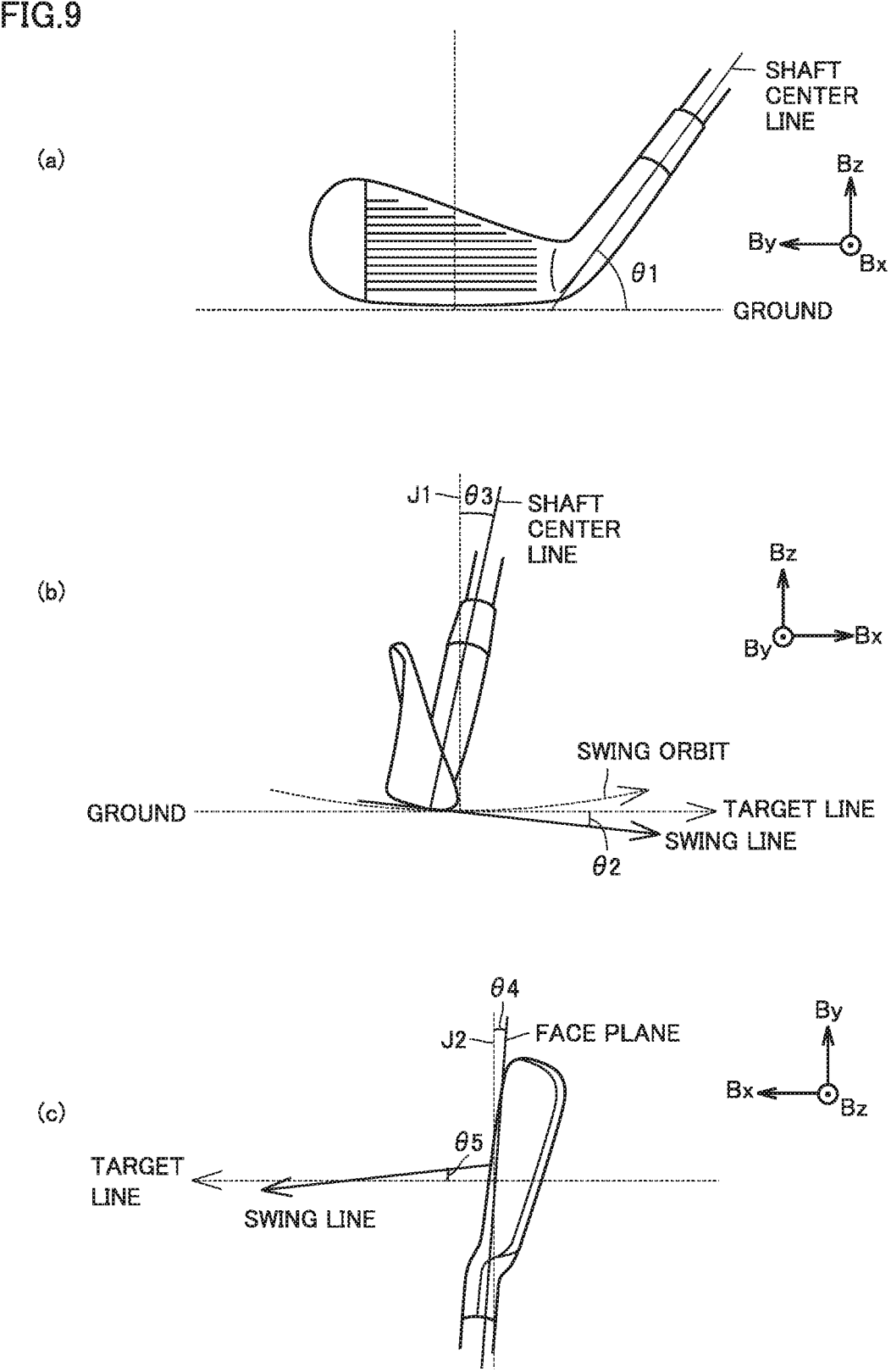
FIG. 9 is a diagram illustrating lie angle, attack angle, shaft lean angle, face angle, and swing path (angle of approach).

FIG. 9 is a diagram illustrating lie angle, attack angle, shaft lean angle, face angle, and swing path (angle of approach). In FIG. 9, a coordinate system is defined such that one axis on the ground (for example, horizontal plane) is the Bx axis, the other axis on the ground normal to the Bx axis is the By axis, and the direction vertical to the Bx axis and the By axis is the Bz axis. The direction (−Bz direction) as viewed from the direction normal to the ground is referred to as a two-dimensional view. The Bx axis is defined as target line direction. The target line direction is, for example, a target direction of the hit ball in the two-dimensional view. Specifically, FIG. 9(a) shows the lie angle at impact. FIG. 9(b) shows the attack angle and the shaft lean angle at impact. FIG. 9(c) is the face angle and the swing path at impact.

Referring to FIG. 9(a), the lie angle at impact is defined as angle θ1 of shaft 52 (specifically, shaft center line) of golf club 50 relative the ground (BxBy plane in the figure).

Referring to FIG. 9(b), the attack angle at impact is defined as angle θ2 formed between the tangent direction (swing line direction) at impact in contact with the swing orbit of the head of golf club 50 projected on a virtual vertical plane (BxBz plane in the figure) normal to the ground and the target line direction projected on the virtual vertical plane. In other words, attack angle θ2 at impact is the angle of the direction of the swing trajectory relative to the ground at impact. In the present embodiment, when the inclination of the swing line has a negative value (the case shown in FIG. 9(b)), the attack angle θ2 has a negative value, whereas when the inclination of the swing line has a positive value, the attack angle θ2 has a positive value. Specifically, in the case of a downward blow in which the head approaches the ball diagonally downward, the attack angle is θ2<0°. In the case of a level blow in which the head approaches the ball horizontally, the attack angle is θ2=0°. In the case of an upper blow in which the head approaches the ball diagonally upward, the attack angle is θ2>0°.

Referring to FIG. 9(b), the shaft lean angle is defined as angle θ3 of shaft 52 relative to a virtual plane J1 normal to the target line direction. In other words, the shaft lean angle θ3 at impact is the angle of shaft 52 relative to the virtual plane J1 normal to the ground at impact. In the present embodiment, when the inclination of the shaft center line has a positive value (the case shown in FIG. 9(b)), the shaft lean angle θ3 has a negative value, whereas when the inclination of the shaft center line has a negative value, the shaft lean angle θ3 has a positive value.

Referring to FIG. 9(c), the face angle at impact is defined as angle θ4 of the face plane of golf club 50 relative to virtual plane J2 orthogonal to the target line direction. In the present embodiment, when the inclination of the face plane has a positive value (in the case shown in FIG. 9(c)), face angle θ4 has a positive value, whereas when the inclination of the face plane has a negative value, face angle θ4 has a negative value.

The swing path at impact (angle of approach) is defined as angle θ5 formed with the target line direction relative to the swing line direction. In the present embodiment, when the inclination of the swing line direction has a positive value (the case shown in FIG. 9(c)), swing path θ5 has a negative value, whereas when the inclination of the swing line direction has a negative value, swing path θ5 has a positive value.

Face angle θ4 represents the inclination of the face plane with reference to the target line direction fixed in orientation irrespective to the direction of approach (swing line direction) to the hit point of the head. On the other hand, the relative face angle representing the inclination of the face plane with reference to the swing line direction (hereinafter also referred to as "relative face angle") is the angle obtained by subtracting swing path θ5 from face angle θ4. The relative face angle may be referred to as the face to path angle.

Referring to FIG. 8 again, swing analysis device 10 corrects the attitude information (attitude angle) of golf club 50 based on the strain information (step S130). Specifically, swing analysis device 10 corrects the lie angle and the attack angle of the attitude angle calculated at step S120, using a predetermined formula and the strain information. The process at step S130, which will be detailed later, is a process for accurately calculating the lie angle and the attack angle at impact, considering the strain of shaft 52 at impact.

Swing analysis device 10 displays swing analysis information including the attitude angle including the corrected lie angle and attack angle and other analysis information (for example, swing tempo) on display 110 (step S140). Swing analysis device 10 accepts an instruction from the user through touch panel 106 and successively displays screens for fitting a golf club suitable for the golfer (step S150).

<Detail of Each Process>

The detail of each process performed in swing analysis system 1000 will be described below.

(Calibration)

As described above, sensor device 20 is attached to shaft 52 of golf club 50. Golf club 50 with sensor device 20 attached thereto is provided to, for example, a golf shop and used for swing analysis for customers coming to the golf shop.

As explained in FIG. 4, sensor device 20 is attached to shaft 52 such that the x axis of the sensor coordinates is set in the longitudinal direction of shaft 52. However, there may be a difference between the x-axis direction of the sensor coordinates and the longitudinal direction of shaft 52, depending on the manner of attachment of sensor device 20. In this case, the attitude angles calculated by swing analysis device 10 have errors by the amount corresponding to the difference.

Then, swing analysis system 1000 according to the present embodiment is configured to perform calibration for suppressing variation of swing analysis performance with individual differences. With golf club 50 with sensor device 20 being fixed, a calibration value corresponding to the difference is calculated. Here, it is assumed that the person (hereinafter simply referred to as "fitter") who makes calibration settings is a person who encourages a customer (here, the golfer who uses golf club 50) to purchase a golf club. The calibration settings may be performed before golf club 50 with sensor device 20 is provided to a golf shop and the like.

Figure 10:
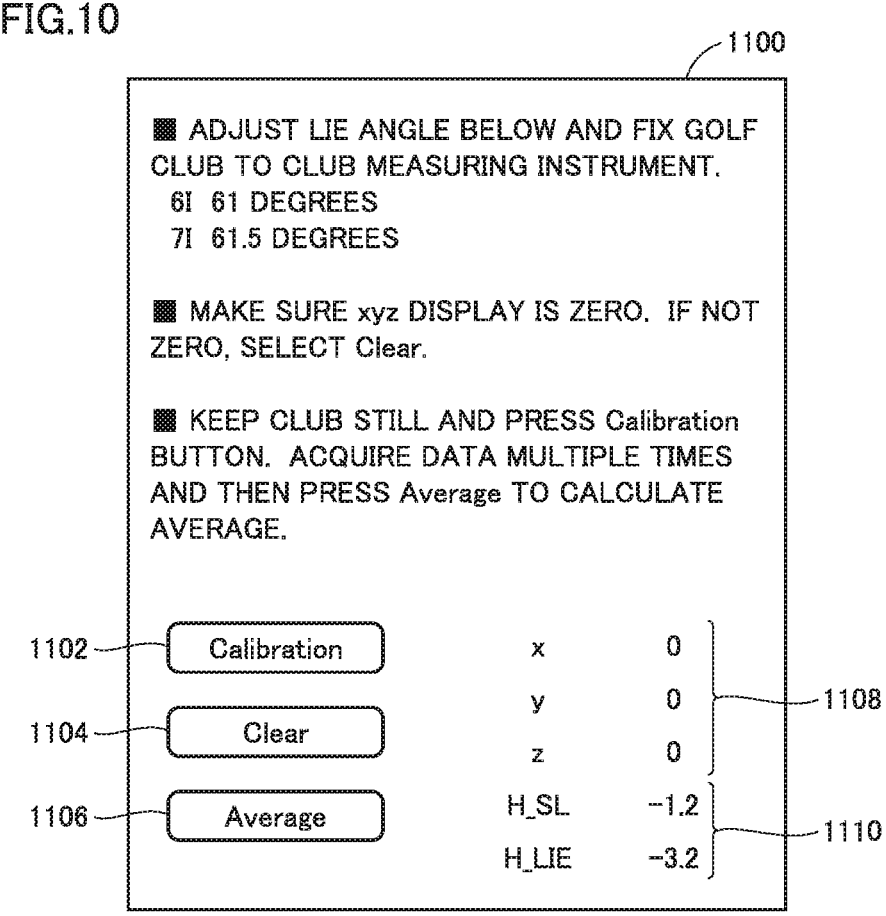
FIG. 10 is a diagram showing an example of a calibration setting screen.
Figure 11:
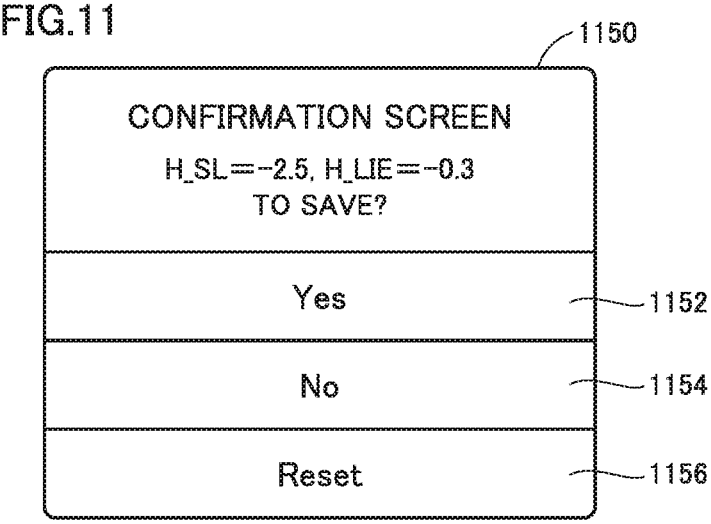
FIG. 11 is a diagram showing an example of a calibration confirmation screen.

FIG. 10 is a diagram showing an example of a calibration setting screen. FIG. 11 is a diagram showing an example of a calibration confirmation screen. Swing analysis device 10 accepts selection on a calibration setting button included in another menu screen (not shown) and then displays a calibration setting screen 1100 as shown in FIG. 9.

Referring to FIG. 10, in accordance with an instruction appearing on calibration setting screen 1100, the fitter fixes golf club 50 with sensor device 20 attached thereto on a club measuring instrument that is a jig placed on a plane parallel to the ground. For example, when a 6-iron is selected as golf club 50, the lie angle of golf club 50 adjusted to 61 degrees is fixed to the club measuring instrument. When a 7-iron is selected as golf club 50, the lie angle of golf club 50 adjusted to 61.5 degrees is fixed to the club measuring instrument. A known measuring instrument (for example, golf club gauge, golf club angle measuring instrument) for use in measuring the dimensions of a golf club head is used as the club measuring instrument.

The fitter makes sure that "x", "y" and "z" appearing in region 1108 are zero. Here, "x", "y" and "z" indicate the acceleration in the x-axis direction, the acceleration in the y-axis direction, and the acceleration in the z-axis direction, respectively, in the sensor coordinate system. If they are not zero, a clear button 1104 is selected to set the accelerations in three axis directions to zero.

"H_LIE" appearing in region 1110 is a calibration value for the lie angle, and "H_SL" is a calibration value for the shaft lean angle. These calibration values H_SL, H_LIE are configured to be stored in memory 204 of sensor device 20. When establishing communication with sensor device 20, swing analysis device 10 reads (receives) calibration values and then displays the read calibration values in region 1110. For example, the initial value of calibration value H_SL is 0, and the initial value of calibration value H_LIE is −1.0.

Next, the fitter selects a calibration button 1102 in a state in which golf club 50 is set still. Swing analysis device 10 accepts the selection on calibration button 1102 and then displays the accelerations in three axis directions acquired from sensor device 20 in region 1108. When accepting the selection on calibration button 1102 again, swing analysis device 10 updates the display values in region 1108 with the accelerations in three axis directions acquired again from sensor device 20.

When accepting the selection on average button 1106, swing analysis device 10 averages a plurality of acceleration data and calculates the lie angle and the shaft lean angle based on the average value. The method of calculating the lie angle and the shaft lean angle will be described later. Swing analysis device 10 calculates calibration values using the calculated lie angle C_LIE and shaft lean angle C_SL.

For example, when golf club 50 is a 7-iron, golf club 50 with the lie angle adjusted to 61.5 degrees is fixed to the club measuring instrument. Therefore, H_LIE=61.5−C_LIE holds. H_SL=0−C_SL also holds.

Upon calculating the calibration values, swing analysis device 10 pops up a confirmation screen 1150 shown in FIG. 11 in the vicinity of the center of calibration setting screen 1100. Confirmation screen 1150 displays the calibration values H_SL, H_LIE and also displays information to prompt the fitter to confirm whether to save the calibration values.

When accepting the selection on a YES button 1152, swing analysis device 10 instructs sensor device 20 to store the calibration values H_SL, H_LIE into an internal memory. Sensor device 20 saves the calibration values in memory 204.

When accepting the selection on a NO button 1154, swing analysis device 10 cancels the calculated average value of a plurality of acceleration data. In this case, the calibration values H_SL, H_LIE are not stored in sensor device 20.

When accepting the selectin on reset button 1156, swing analysis device 10 instructs sensor device 20 to set the calibration values H_SL, H_LIE to the initial values. Sensor device 20 saves the initial values of the calibration values in memory 204.

When at least one of the calibration values H_SL, H_LIE does not fall within a predetermined range (for example, in the range from −5 degrees to +5 degrees), swing analysis device 10 may display an alert screen to indicate that the calibration values are abnormal. In this case, the calibration values H_SL, H_LIE are not saved in sensor device 20.

When establishing communication with sensor device 20, swing analysis device 10 reads the calibration values set as described above and corrects the attitude angle information based on the calibration values. This can suppress variation of swing analysis performance with individual differences.

(Standstill Detection)

Here, the method of detecting a standstill state immediately before a swing is described. When the user swings a golf club, the following procedure is generally performed. Specifically, the user grips a golf club, takes an address posture, and then performs a swing operation to hit the golf ball.

Swing analysis device 10 calculates swing analysis information in time series based on the sensor data (for example, acceleration information and angular rate information) acquired from sensor device 20. For example, if preparation for a swing (for example, waggling) is set as the swing start point time, integration errors and the like are accumulated and appropriate swing analysis information may fail to be obtained. It is therefore necessary to accurately detect a standstill state immediately before a swing (that is, swing start point time).

Figure 12:
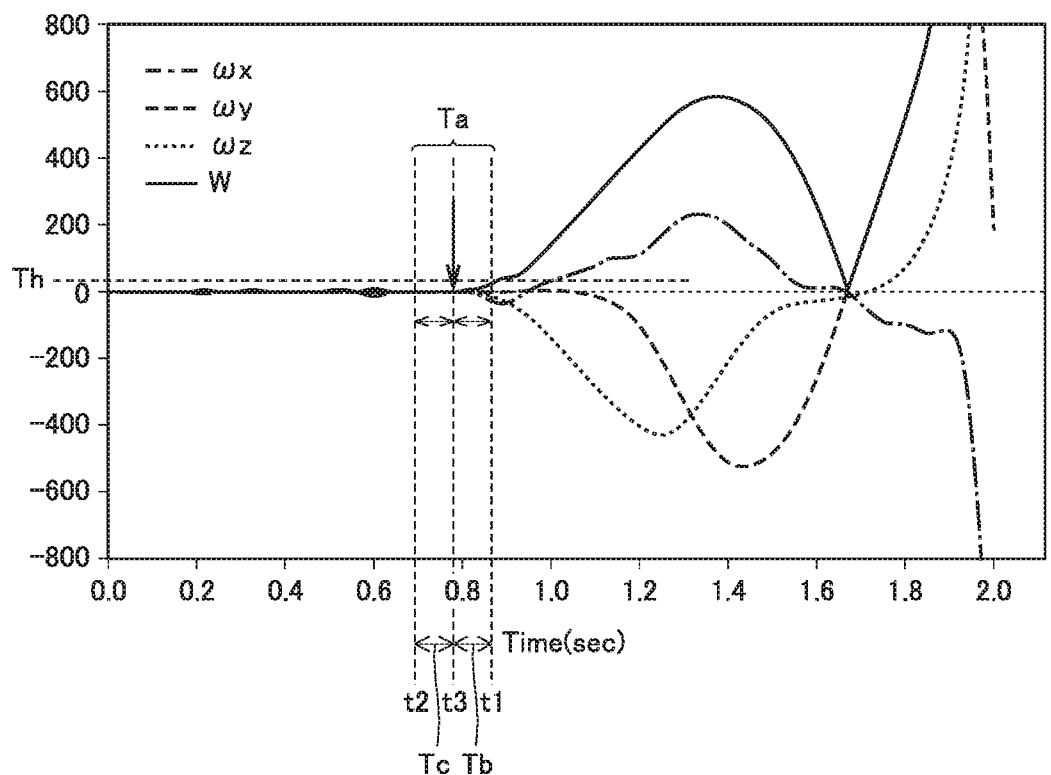
FIG. 12 is a diagram illustrating a standstill detection method.

FIG. 12 is a diagram illustrating a standstill detection method. In FIG. 12, the horizontal axis represents time T (s), and the vertical axis shows the angular rates (deg/s) about three axes (sensor coordinate system) orthogonal to each other and the combined angular rate.

The graph shown in FIG. 12 shows angular rate information when the user swings golf club 50 and hits the ball. Swing analysis device 10 calculates time t1 when the combined angular rate W is less than a reference threshold Th (for example, 20 deg/s), back to the time before the impact time by a predetermined amount of time (for example, 0.5 second).

Letting the angular rate about the x axis be ωx, the angular rate about the y axis be ωy, and the angular rate about the z axis be ωz, the combined angular rate W is written as Equation (1) below.

$$W = \sqrt{\omega_x^2 + \omega_y^2 + \omega_z^2} \quad (1)$$

The impact time will now be described. At impact, a signal of acceleration sensor 206 in sensor device 20 makes a transient response due to the impact of hitting a ball, and therefore the acceleration abruptly changes. Then, swing analysis device 10 calculates the time when the amount of change per unit time of the combined acceleration AC is equal to or greater than a threshold (for example, 500), as the impact time.

Letting the acceleration in the x-axis direction be ax, the acceleration in the y-axis direction be ay, and the acceleration in the z-axis direction be az, the combined acceleration AC is written as Equation (2) below.

$$AC = \sqrt{a_x^2 + a_y^2 + a_z^2} \quad (2)$$

Swing analysis device 10 calculates period Tc from time t2 prior to the calculated time t1 by the amount of time Ta (for example, 0.2 second) to time t3 prior to time t1 by the amount of time Tb (for example, −0.1 second), as the period during which the user is standing still (standstill period).

(Calculation of Attitude Angle)

Swing analysis device 10 calculates the attitude information of sensor device 20, based on the acceleration information and the angular rate information. Here, direction cosine matrix Rq that is the attitude information of sensor device 20 is written as Equation (3) below.

$$Rq = \begin{pmatrix} a_{11} & a_{12} & a_{13} \\ a_{21} & a_{22} & a_{23} \\ a_{31} & a_{32} & a_{33} \end{pmatrix} \quad (3)$$

As shown in FIG. 4, the x axis in the sensor coordinate system (local coordinate system) is set in the longitudinal direction of shaft 52. Therefore, the attitude angle of golf club 50 can be calculated using the attitude information (that is, direction cosine matrix Rq) of sensor device 20. Specifically, the lie angle A_LIE, the shaft lean angle A_SL, and the face angle A_FA of golf club 50 can be respectively written as Equation (4), Equation (5), and Equation (6) below, using the elements of the direction cosine matrix Rq.

$$A\_LIE = \frac{180}{\pi} \times \arctan\left(\frac{-a_{31}}{a_{11}}\right) \quad (4)$$

$$A\_SL = \frac{180}{\pi} \times \arctan\left(\frac{a_{21}}{-a_{31}}\right) \quad (5)$$

$$A\_FA = \frac{180}{\pi} \times \arctan\left(\frac{a_{12}}{a_{22}}\right) \quad (6)$$

Swing analysis device 10 (processor 102) averages the time-series acceleration information (accelerations in three axis directions) in standstill period Tc and calculates a direction cosine matrix Rq0 that is the initial attitude of sensor device 20, based on the averaged acceleration information. Processor 102 calculates the initial values of the lie angle A_LIE, the shaft lean angle A_SL, and the face angle A_FA (that is, initial attitude angles), using the direction cosine matrix Rq0 and Equations (4) to (6) above. Processor 102 sets time t3 in FIG. 12 as the swing start time.

Processor 102 calculates the direction cosine matrix Rq in time series in the swing period from the swing start time to the impact time. The direction cosine matrix Rq is calculated in time series generally through the procedure below.

The acceleration information of the sensor coordinate system is converted into acceleration information (acceleration vector) in the global coordinate system, using the direction cosine matrix Rq. Subsequently, a vector r (sensor coordinate system) from sensor device 20 to the head center of golf club 50 is converted into the global coordinate system, using the direction cosine matrix Rq.

Next, a rotation unit vector u in the sensor coordinate system and a rotation angle α per unit are calculated, based on the angular rates about the three axes. The rotation unit vector u in the sensor coordinate system is converted into the global coordinate system, using the direction cosine matrix Rq, and an angular rate vector ωg in the global coordinate system is calculated using the rotation unit vector ug and the rotation angle α converted into the global coordinate system.

Next, a transformation matrix R is found using Rodrigues' rotation formula for the rotation unit vector ug. Then, a direction cosine matrix Rq1 is calculated by rotating the direction cosine matrix Rq using the transformation matrix R. The process described above is repeated using the direction cosine matrix Rq1. The direction cosine matrix Rq is thus calculated in time series.

On the other hand, processor 102 integrates the acceleration information (acceleration vector) in the global coordinate system with respect to time to calculate the velocity information (velocity vector V) of sensor device 20 in the global coordinate system. Processor 102 calculates a head velocity vector Vh, based on the velocity vector V, the angular rate vector ωg, and the vector r from sensor device 20 to the head center in the global coordinate system. Letting an element X, an element Y, and an element Z of the head velocity vector Vh be Vhx, Vhy, and Vhz, the head speed Vhs is written as Equation (7) below.

$$Vhs = \sqrt{Vh_x^2 + Vh_y^2 + Vh_z^2} \tag{7}$$

The attack angle A_AT and the swing path SWP of golf club 50 are respectively written as Equation (8) and Equation (9) below, using the elements of the velocity vector V.

$$A\_AT = \frac{180}{\pi} \times \arctan\left(\frac{Vh_z}{Vh_y}\right) \tag{8}$$

$$SWP = \frac{180}{\pi} \times \arctan\left(\frac{Vh_x}{Vh_y}\right) \tag{9}$$

Then, the lie angle Lc, the shaft lean angle SLc, and the face angle FAc at impact are calculated based on the direction cosine matrix Rqi at impact and Equations (4) and (5). The attack angle ATc and the swing path SWc at impact are calculated based on the velocity vector V at impact and Equations (8) and (9). The relative face angle Frc at impact corresponds to the value obtained by subtracting the swing path SWc from the face angle FAc.

(Correction of Attitude Angle)

The method of correcting the attitude angle calculated as described above using the strain information will be described. As shown in FIG. 6 and FIG. 7, at impact when the golf club is swung down, strain occurs in the toe down direction Ey and the hit ball direction Ex of shaft 52.

The attitude angle calculated by the method above is obtained assuming that the head of golf club 50 is located along the center axis line P of shaft 52. Thus, the calculated attitude angle is thought to have a slight error from the actual attitude angle at impact. Then, swing analysis device 10 according to the present embodiment corrects the calculated attitude angle using strain information.

The inventor of the subject application has conducted elaborate studies and has found that, of the attitude angles, the lie angle (the angle corresponding to θ1 in FIG. 9) and the shaft lean angle (the angle corresponding to θ3 in FIG. 9) are significantly affected by strain of shaft 52. Specifically, 18 golfers played in total 42 shots, and the relation of the actually measured values of the lie angle and the shaft lean angle to the strain amount was evaluated.

The inventor of the subject application has made elaborate studies based on this evaluation and has found that the strain amount in the toe down direction Ey of shaft 52 has a high correlation to the actually measured value of the lie angle. The inventor of the subject application has also found that the strain amount in the hit ball direction Ex of shaft 52, the face angle, and the swing path particularly have a high correlation to the actually measured value of the shaft lean angle.

Then, based on the finding above, the inventor of the subject application has conducted multiple regression analysis, where the lie angle Lc at impact calculated by the method described above and the strain amount Dy in the toe down direction Ey at impact are explanatory variables, and the actually measured value of the lie angle at impact is an object variable. The resulting regression equation is written as Equation (10), where a0, a1, a2 are multiple regression coefficients. The lie angle La is the calculated value of the object variable.

$$La = a1 \times (Dy) + a2 \times Lc + a0 \tag{10}$$

Equation (10) can be used to obtain the lie angle La that is the calculated value of the object variable (that is, the actually measured lie angle), based on the lie angle Lc at impact and the strain amount Dy in the toe down direction Ey at impact. Therefore, correction can be performed such that the lie angle Lc further approaches the actually measured value. Hereinafter, the lie angle La that is the value obtained by correcting the lie angle Lc using Equation (10) may be referred to as the corrected value of the lie angle. The validity of the multiple regression equation shown in Equation (10) is as shown in FIG. 13.

Figure 13:
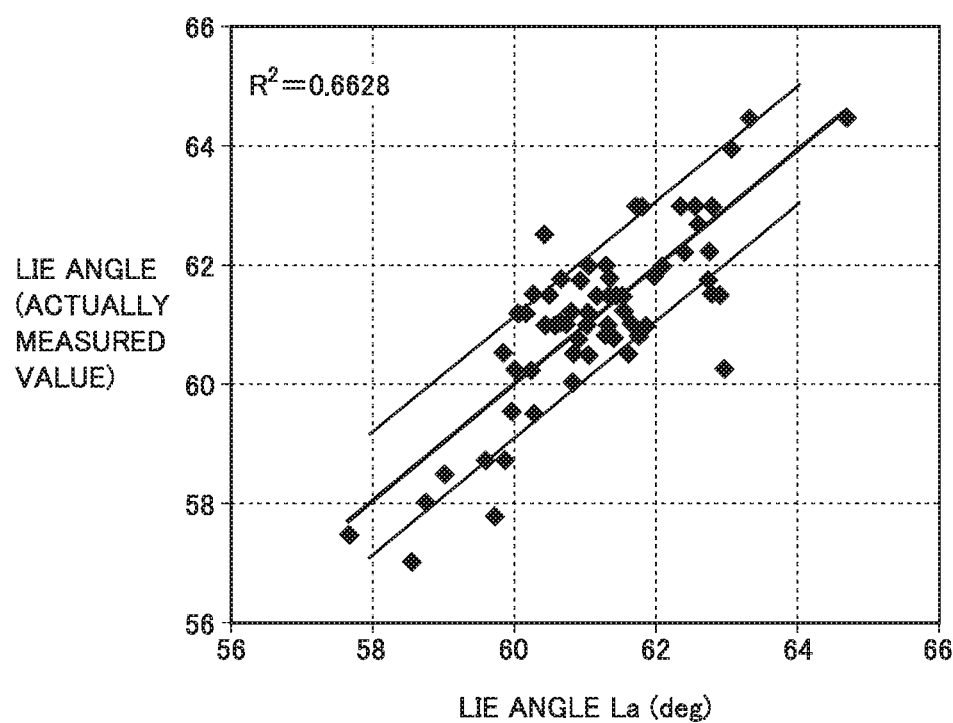
FIG. 13 is a diagram illustrating the validity of a multiple regression equation obtained by regression analysis.

FIG. 13 is a diagram illustrating the validity of the multiple regression equation obtained by regression analysis. Specifically, the horizontal axis shows the corrected value La of the lie angle calculated using Equation (10), and the vertical axis shows the actually measured value of the original lie angle. Referring to FIG. 13, as the determination coefficient $R^2$ of the multiple regression equation shown in Equation (10) is 0.6628, a high determination coefficient is obtained, showing validity of the finding obtained by the inventor of the subject application through elaborate studies.

Similarly, based on the finding above, the inventor of the subject application has conducted multiple regression analysis, where the shaft lean angle SLc at impact calculated by the method above, the face angle FAc, the swing path SWc, the strain amount Dx in the hit ball direction Ex at impact calculated by the method above are explanatory variables, and the actually measured value of the shaft lean angle at impact was an object variable. The resulting regression equation is shown by Equation (11) below, where b0, b1, b2, b3 are multiple regression coefficients. The shaft lean angle SLa is the calculated value of the object variable.

$$SLa = b1 \times (Dx) + b2 \times (FAc + SWc) + b3 \times SLc + b0 \tag{11}$$

Equation (11) can be used to obtain the shaft lean angle SLa that is the calculated value of the object variable (that is, the actually measured shaft lean angle), based on the shaft lean angle SLc, the face angle FAc, the swing path SWc at impact, and the strain amount Dx in the hit ball direction Ex at impact. Thus, correction can be performed such that the shaft lean angle SLc further approaches the actually measured value. Hereinafter, the shaft lean angle SLa that is the value obtained by correcting the shaft lean angle SLc using Equation (11) may be referred to as the corrected value of the shaft lean angle. As the determination coefficient $R^2$ of the multiple regression equation shown in Equation (11) is 0.8102, a high determination coefficient is obtained, showing validity of the finding obtained by the inventor of the subject application through elaborate studies.

The final lie angle Lf, shaft lean angle SLf, attack angle ATf, and relative face angle Frf at impact considering the calibration values are respectively written as Equation (12), Equation (13), Equation (14), and Equation (15).

$$Lf = La + H\_LIE \tag{12}$$

$$SLf = SLa + H\_SL \tag{13}$$

$$ATf = ATc + H\_SL \tag{14}$$

$$Frf = Frc + H\_SL \tag{15}$$

In this way, the final lie angle Lf is the value obtained by correcting the lie angle Lc calculated based on the acceleration information and the angular rate information, based on the strain amount Dy and the calibration value H_LIE. The final shaft lean angle SLf is the value obtained by correcting the shaft lean angle SLc calculated based on the acceleration information and the angular rate information, based on the strain amount Dx and the calibration value H_SL.

(Fitting)

Here, the procedure for fitting a golf club suitable for the user will be described. In the following description, it is assumed that the user of swing analysis device 10 is the fitter. It is also assumed that golf club 50 is a 7-iron.

The fitter selects an icon appearing on display 110 to give an instruction to start a swing analysis application. Swing analysis device 10 accepts the start instruction and displays a login screen to accept input of predetermined user ID and password. If login authentication is successful, swing analysis device 10 displays a top screen 1200.

Figure 14:
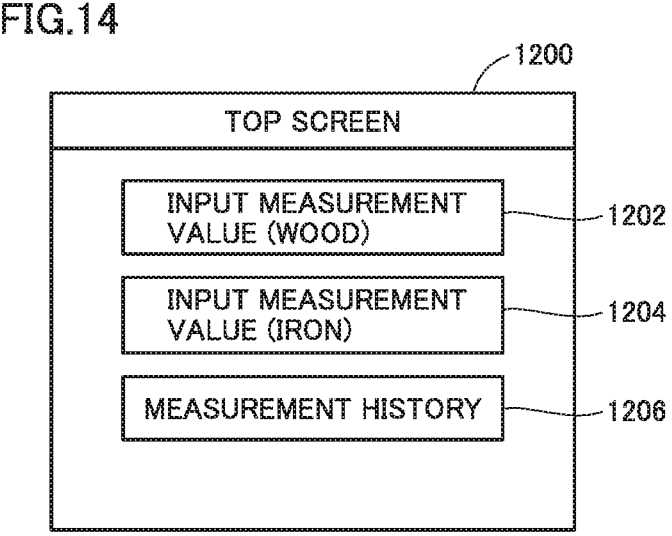
FIG. 14 is a diagram showing an example of a top screen.

FIG. 14 is a diagram showing an example of the top screen. Referring to FIG. 14, top screen 1200 includes a button 1202 for accepting input of the measured value of a wood, a button 1204 for accepting input of the measured value of an iron, and a button 1206 for displaying the past measurement history. In the present embodiment, button 1204 is selected.

When accepting the selection on button 1204, swing analysis device 10 establishes communication with sensor device 20. Typically, swing analysis device 10 is paired with sensor device 20. When pairing is finished, swing analysis device 10 displays an input screen for various information about the user. Here, swing analysis device 10 reads the calibration values described above.

FIG. 15 is a diagram showing an example of an input screen 1250 for various information. Referring to FIG. 15, swing analysis device 10 accepts information including the user's name, age, gender, email address, height, dominant hand, average score, the average number of rounds, and the fitter's name through touch panel 106.

FIG. 16 is a diagram showing an example of a measurement screen. Referring to FIG. 16, measurement screen 1300 includes a result region 1302 for displaying the measurement results, a start button 1304 for starting measurement, a button 1306 for cancelling measurement, a transition button 1308 for making a transition to a wood shaft recommend screen, and a transition button 1310 for making a transition to an iron shaft recommend screen.

When accepting start button 1304, swing analysis device 10 gives a message such as "Stay still", "Play a shot" to the user. In response to the message, the user takes an address posture and then makes a swing operation to hit the golf ball using golf club 50 with sensor device 20 mounted thereon.

Swing analysis device 10 executes a swing analysis process based on various information received from sensor device 20 and displays the analysis results as measurement results. Specifically, result region 1302 shows "head speed" at impact, "swing tempo" indicating the maximum amount of deflection during a swing, "kick angle" at impact, "toe down amount" at impact, "release factor" at impact, "lie angle" at impact, "shaft lean angle" at impact, "attack angle" at impact, and "relative face angle" at impact. The head speed, the lie angle, the shaft lean angle, the attack angle, and the relative face angle are calculated using the method described above. To simplify the explanation for customers, the relative face angle is simply displayed as "face angle". This is applicable to the screens described below.

The measurement values of swing tempo, kick angle, toe down amount, and release factor are calculated using strain sensor 210 by sensor device 20. The calculation method of swing tempo, kick angle, and the toe down amount are disclosed, for example, in Japanese Patent Laying-Open No. 2010-187749. The calculation method of release factor is disclosed as a method of calculating an expected bending point value in Japanese Patent Laying-Open No. 2010-187749.

FIG. 16 shows a situation in which analysis of a first swing motion is conducted by the user and the measurement results are displayed. Every time the user makes a swing, the measurement result is added. The average value of measurement results is also displayed. When the user finishes swings, the fitter selects a transition button 1310.

FIG. 17 is a diagram showing an example of an iron shaft recommend screen. Referring to FIG. 17, iron shaft recommend screen 1350 includes a region 1352 for displaying measurement values serving as elements for selecting an iron shaft, a region 1354 for displaying a shaft recommended by the fitter, a region 1356 for displaying a steel shaft suitable for the user, a region 1358 for displaying a graphite shaft suitable for the user, a transition button 1360 for making a transition to the top screen, a button 1362 for going back to the previous screen, and a transition button 1364 for making a transition to an iron head recommend screen.

Region 1352 displays the measurement values of the user (black dots in the figure) and displays the average values of an average golfer (hatched parts in the figure). The user can promptly grasp his/her own position relative to the average.

Region 1356 displays a steel shaft selected by swing analysis device 10, based on head speed, swing tempo, toe down amount, kick angle, and release factor. Region 1356 indicates that the most suitable steel shaft is "shaft ST1". Similarly, region 1358 indicates that the most suitable graphite shaft is "shaft G1". When the selection of an iron shaft is finished, the fitter selects transition button 1364.

Figure 18:
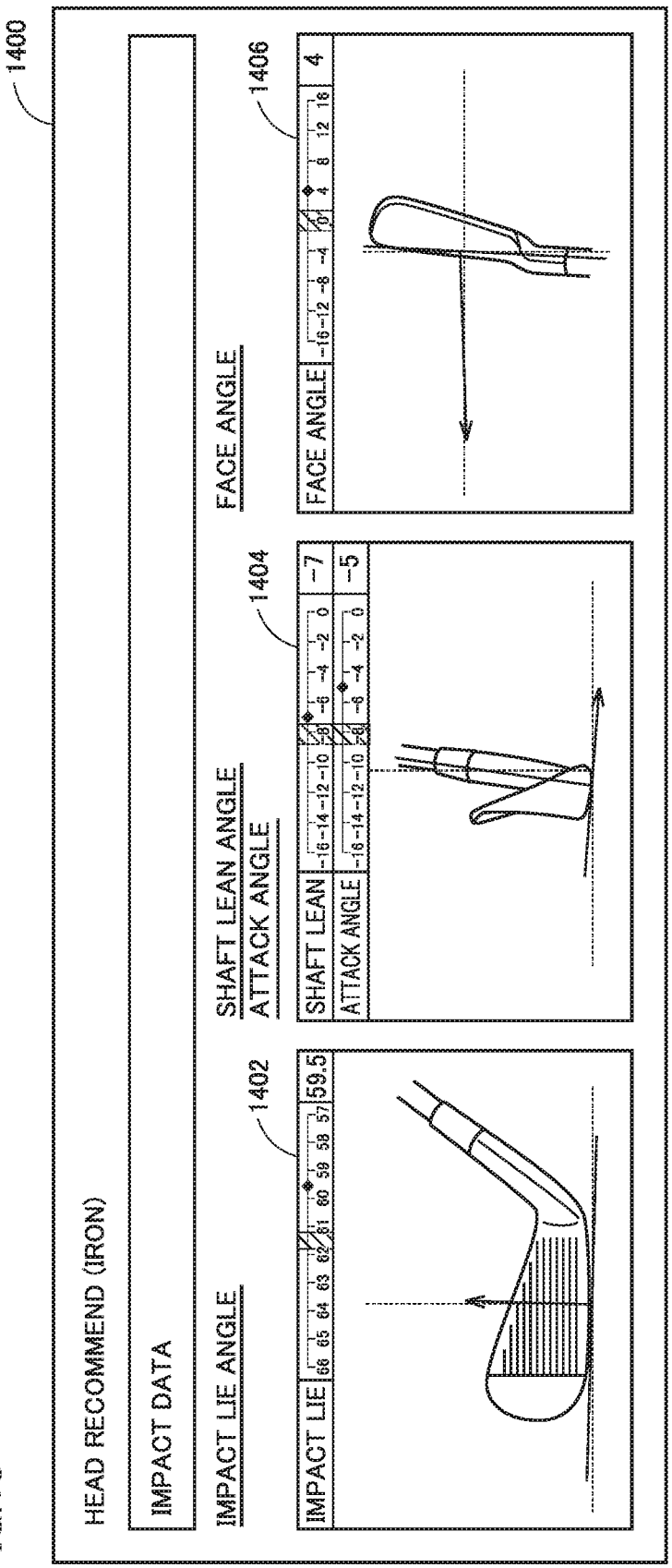
FIG. 18 is a diagram showing an example of an iron head recommend screen.
Figure 19:
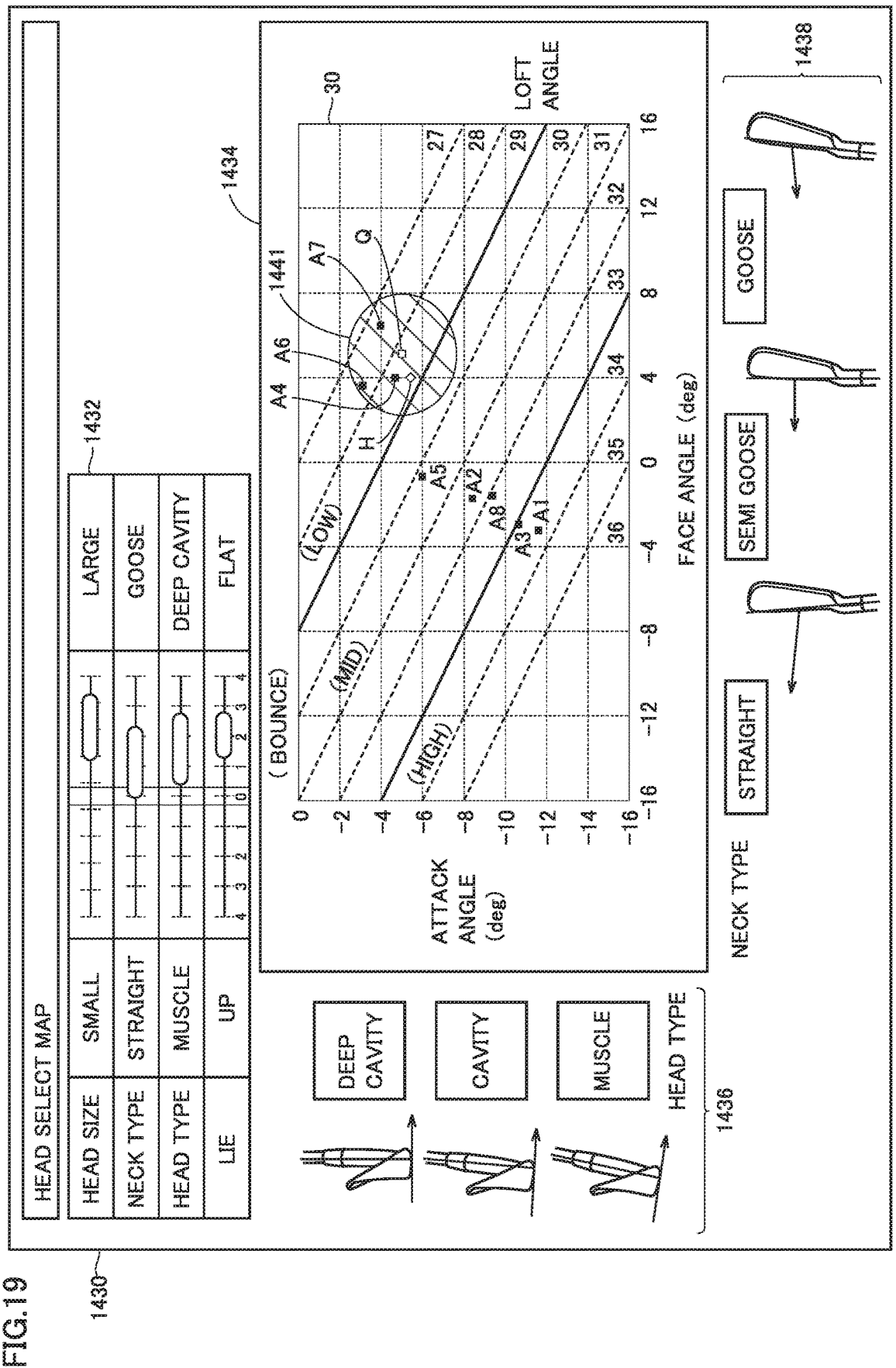
FIG. 19 is a diagram showing an example of an iron head recommend screen.
Figure 20:
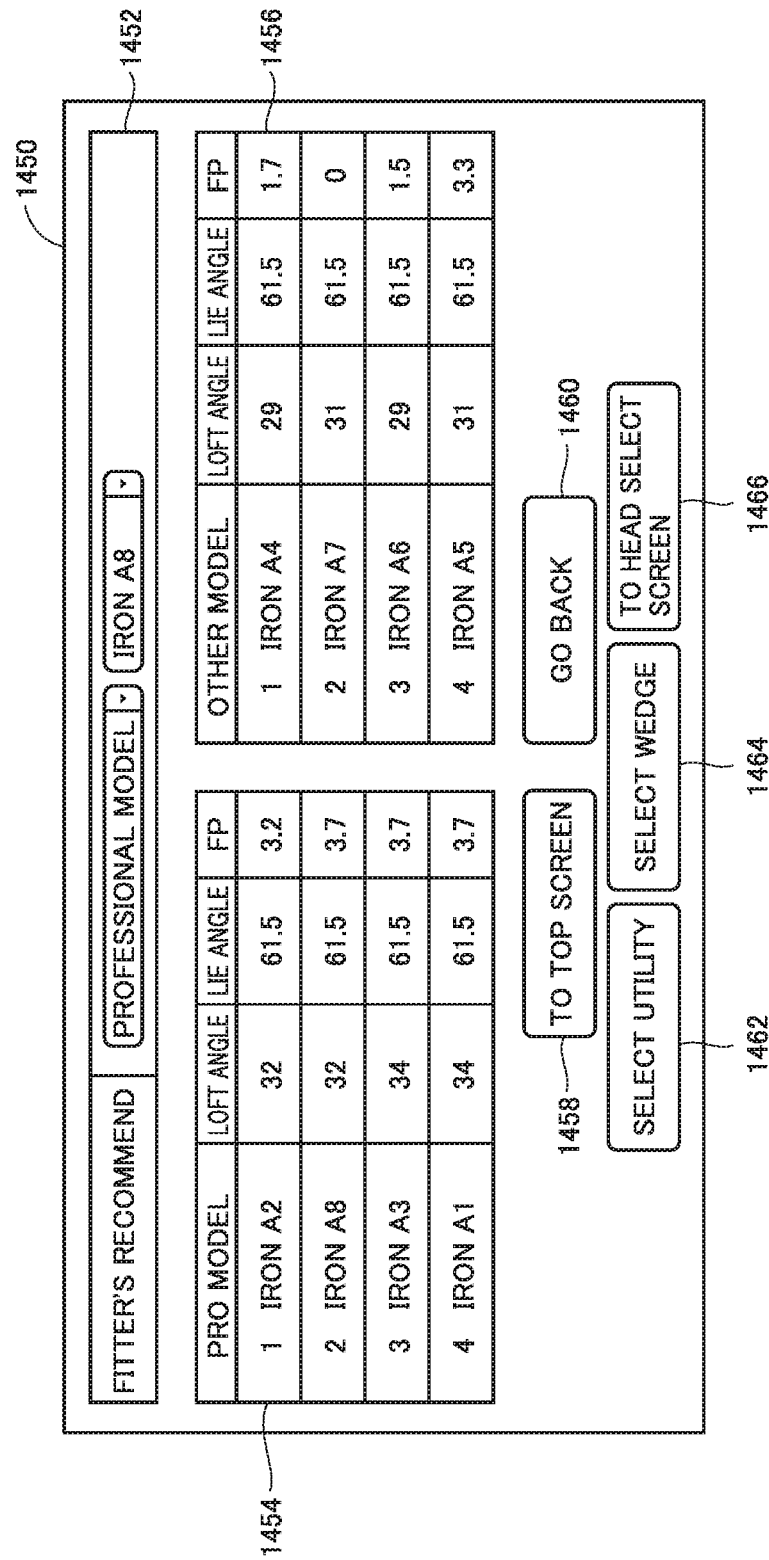
FIG. 20 is a diagram showing an example of an iron head recommend screen.

FIG. 18, FIG. 19, and FIG. 20 are diagrams showing an example of the iron head recommend screen. Specifically, FIG. 18 is a diagram showing a screen region 1400 for displaying the attitude angle at impact. FIG. 19 is a diagram showing a screen region 1430 showing a head select map. FIG. 20 is a diagram showing a screen region 1450 for displaying a head suitable for the user. The iron head recommend screen includes screen regions 1400, 1430, 1450, and these screen regions are displayed by scrolling the iron head recommend screen up and down.

Referring to FIG. 18, screen region 1400 includes a region 1402 for displaying the lie angle at impact, a region 1404 for displaying the shaft lean angle and the attack angle at impact, and a region 1406 for displaying the face angle at impact (and swing path). The golfer can view screen region 1400 to imagine the states of lie angle, shaft lean angle, attack angle, face angle, and swing path at impact.

Regions 1402 to 1406 each show the user's own measurement value (black dot in the figure) and also shows a common average value (hatched part in the figure). This allows the user to promptly grasp his/her own position relative to the average.

Referring to FIG. 19, screen region 1430 includes a region 1432 for displaying spec information of the iron head recommended for the user, a region 1434 for displaying an iron model recommended for the user, a region 1436 for displaying the relation between head type and attack angle, and a region 1438 for displaying the relation between neck type and relative face angle.

Specifically, region 1432 shows information including head size, neck type, head type, and lie angle recommended for the user. In the example in FIG. 19, "large" head size is recommended rather than "small", "goose" neck type is recommended rather than "straight", "deep cavity" head type is recommended rather than "muscle", and "flat" lie angle is recommended rather than "up".

Region 1434 shows a map 30 for selecting an iron model recommended for the user, based on attack angle, relative face angle, shaft lean angle, head speed, and variation (standard deviation) of head speed.

The horizontal axis in map 30 shows the relative face angle at impact, as a typical example of the index of flight characteristics in the right/left direction of the hit ball at impact. The relative face angle at impact large in positive direction (that is, the orientation of the face is open relative to the swing trajectory) causes slice spin and a ball trajectory curving to the right. On the other hand, the face angle at impact large in negative direction (that is, the orientation of the face is closed relative to the swing trajectory) causes hook spin and a ball trajectory curving to the left.

In general, the "goose" type is a neck type that is likely to impart hook spin. Therefore, in region 1438, the characters "goose", which is a recommended neck type, appears in the vicinity of an image indicating that the orientation of the face is open relative to the swing trajectory (that is, swing likely to impart slice spin).

The "straight" type is a neck type that is likely to impart slice spin. Thus, in region 1438, the characters "straight", which is a recommended neck type, appears in the vicinity of an image indicating that the orientation of the face is closed relative to the swing trajectory (that is, a swing likely to impart hook spin).

The vertical axis in map 30 shows the attack angle at impact as a typical example of the index of flight characteristics in the up/down direction of the hit ball at impact. The attack angle at impact large in positive direction (that is, a swing trajectory of level blow) causes a high ball trajectory (likely high ball trajectory). On the other hand, the attack angle at impact large in negative direction (that is, a swing trajectory of downward blow) causes a low ball trajectory (less likely high ball trajectory).

In general, the "deep cavity" type is a type focusing on a flight distance. Therefore, in region 1436, the characters "deep cavity", which is a recommended head type, appears in the vicinity of an image indicating a swing trajectory of level blow (that is, a swing trajectory with a high ball trajectory in which the ball goes too high and flies a shorter distance).

The "muscle" type is a head type focusing on control. Therefore, in region 1436, the characters "muscle", which is a recommended head type, appears in the vicinity of an image indicating a swing trajectory of downward blow (that is, a swing trajectory with a low ball trajectory).

Points A1 to A8 in map 30 indicate the models of a plurality of iron clubs with different specs. Points A1 to A8 in map 30 correspond to iron clubs A1 to A8, respectively. Points A1 to A8 are mapped based on the spec information of the iron clubs. Specifically, for each iron club, a right/left index value for the flight characteristics in the right/left direction of the hit ball and an up/down index value for the flight characteristics in the up/down direction of the hit ball are calculated. The right/left position in map 30 is determined based on the right/left index value, and the up/down position in map 30 is determined based on the up/down index value.

For example, the right/left index value Irf is written as Equation (16) below using center of gravity depth Ge, face progression FP, center of gravity distance Gi, and right/left moment of inertia Mrf, where c0, c1, c2, c3, c4 are coefficients.

$$Irl = c1 \times Ge + c2 \times FP + c3 \times Gi + c4 \times Mrl + c0 \quad (16)$$

The up/down index value Iud is written as Equation (17) below, using center of gravity depth Ge, loft angle Lo, sweet spot height SS, and up/down moment of inertia Mud, where d0, d1, d2, d3, d4 are coefficients.

$$Iud = d1 \times Ge + d2 \times Lo + d3 \times SS + d4 \times Mud + d0 \quad (17)$$

As a typical example, iron club A1 is compared with iron club A7. Iron club A1 is located near the lower left in map 30. Thus, iron club A1 is a club suitable for a golfer having swing characteristics of having a tendency of hook spin, curving to the left, and low ball trajectory. In other words, iron club A1 is a club having a tendency of slice spin, curving to the right, and high ball trajectory.

On the other hand, iron club A7 is located near the upper right in map 30. Thus, iron club A7 is a club suitable for the user who has swing characteristics of a tendency of slice spin, curving to the right, and high ball trajectory. In other words, iron club A7 is a club having a tendency of hook spin, curving to the left, and low ball trajectory.

Point H in map 30 indicates the measurement values of relative face angle and attack angle at impact (specifically, the relative face angle Frf and the attack angle ATf). A circle region 1441 (hatched part in map 30) is drawn, considering all of the relative face angle, the attack angle, the shaft lean angle, the head speed, and variation (standard deviation) of the head speed. Therefore, circle region 1441 serves as information suggesting a golf club suitable for the user.

For example, in the example in FIG. 19, it is suggested that iron clubs A4, A6, A7 included in circle region 1441 are models suitable for the user. More specifically, in map 30, of the points (for example, points A1 to A8) indicating the models of iron clubs, the point (in this case, point A4) closest to the center point Q of circle region 1441 is the club most suitable for the user.

The loft angle recommended for the user can also be determined from map 30. For example, the center point of circle region 1441 is present between the dotted line of loft angle of 28 degrees and the dotted line of loft angle of 29 degrees, and then the loft angle 28 degrees or 29 degrees is recommended.

Region 1432 shows information including head size, neck type, head type and lie angle recommended for the user. Circle region 1441 is located at relatively upper right in map 30. Therefore, the neck type "goose" is recommended rather than "straight", and the head type "deep cavity" is recommended rather than "muscle".

The head size is determined by the recommended loft angle. As the recommended loft angle is closer to 27 degrees, a "large" head size is recommended. As the recommended loft angle is closer to 36 degrees, a "small" head size is recommended. In the example in FIG. 19, since the recommended loft angle is 28 degrees or 29 degrees, a relatively "large" head size is recommended.

For the lie angle, when the measurement value of the lie angle at impact is smaller than a reference angle (for example, 61.5 degrees), a "flat" lie angle is recommended. On the other hand, when the measurement value of the lie angle at impact is larger than the reference angle, an "up" lie angle is recommended.

Here, the method of drawing circle region 1441 will be described. As described above, circle region 1441 is drawn based on the relative face angle, the attack angle, the shaft lean angle, the head speed, and variation (standard deviation) of the head speed. Specifically, circle region 1441 is an internal region of a circle having a predetermined radius from the center point Q. The radius is set as desired by, for example, the fitter. The right/left recommended value Krl (that is, the right/left index value recommended for the user) that is the coordinates in the right/left direction of the center point Q is written as Equation (18) below, using the relative face angle at impact Frf, the head speed Vhs at impact, and the standard deviation Vsd of the head speed Vhs that affect the flight characteristics in the right/left direction of the hit ball.

$$Krl = e1 \times Frf + e2 \times Vhs + e3 \times Vsd + e0 \quad (18)$$

Here, e0 to e3 are coefficients. The coefficients e0 to e3 are set such that the center point Q shifts rightward in map 30 as the relative face angle Frc increases in positive direction, the center point Q shifts leftward in map 30 as the head speed Vhs increases, and the center point Q shifts rightward in map 30 as the standard deviation Vsd increases.

The up/down recommended value Kud (that is, the up/down index value recommended for the user) that is the coordinates in the up/down direction of the center point Q is written as Equation (19) below, using the attack angle ATf at impact, the shaft lean angle SLf, the head speed Vhs at impact, and the standard deviation Vsd that affect the flight characteristics in the up/down direction of the hit ball.

$$Kud = f1 \times ATf + f2 \times SLf + f3 \times Vhs + f4 \times Vsd + f0 \quad (19)$$

Here, f0 to f4 are coefficients. The coefficients f0 to f4 are set such that the center point Q shifts upward in map 30 as the attack angle ATf and the shaft lean angle SLf increase in positive direction, the center point Q shifts downward in map 30 as the head speed Vhs increases, and the center point Q shifts upward in map 30 as the standard deviation Vsd increases.

In brief, the center point Q shifts rightward in map 30 as the relative face angle Frf increases in positive direction. The center point Q shifts upward in map 30 as the attack angle ATf and the shaft lean angle SLf increase in positive direction. The center point Q shifts toward the lower left in map 30 as the head speed Vhs increases. The center point Q shifts toward the upper right in map 30 as the standard deviation Vsd increases.

The reason why the center point Q shifts toward the lower left in the map as the head speed Vhs increases is based on the finding as follows. Specifically, it has been found that the golfer with a high head speed is an expert, the attack angle is large in negative direction (strong tendency to downward blow), and the face angle is large in negative direction (strong tendency that the orientation of the face is closed relative to the swing trajectory).

The reason why the center point Q shifts toward the upper right in the map as the standard deviation Vsd of the head speed increases is based on the finding as follows. Specifically, it has been found that a golfer with a large standard deviation of head speed is a beginner or intermediate level, the attack angle is large in positive direction (strong tendency to level blow), and the face angle is large in positive direction (strong tendency that the orientation of the face is open relative to the swing trajectory).

Referring to FIG. 20, screen region 1450 includes a region 1452 for displaying a golf club recommended by the fitter, a region 1454 for displaying an iron club of a professional model suitable for the user, a region 1456 for displaying an iron club of a common model suitable for the user, a transition button 1458 for making a transition to the top screen, a button 1460 for going back to the previous screen, a transition button 1462 for making a transition to a utility select screen, a transition button 1464 for making a transition to a wedge select screen, and a transition button 1466 for making a transition to an iron head select screen.

Region 1454 shows that the iron of the most suitable model is "iron club A2". Similarly, region 1456 displays that the iron of the most suitable common model is "iron club A4". Next, the transition button 1466 is selected to make a transition to the iron head select screen shown in FIG. 21.

FIG. 21 is a diagram showing an example of the iron head select screen. Specifically, the iron head recommend screen shown in FIG. 18 to FIG. 20 is viewed, and the model of iron head (for example, iron A7) is selected to display the screen in FIG. 21. Referring to FIG. 21, a head select screen 1500 includes a region 1502, a region 1504, a button 1506 for going back to the previous screen, and a transition button 1508 for making a transition to a shaft select screen.

Region 1502 is the same as region 1432 in FIG. 19. Region 1504 shows numbers of irons and parameters of a pitching wedge (for example, the length of the shaft, loft angle, lie angle) and also shows the corresponding predicted flight distance. The user can select the number he/she wants to purchase or can change the parameters. In the example in FIG. 21, 4-iron is excluded from purchase targets. The predicted flight distance for each number is calculated by simulation.

The flight distance is determined by hit ball initial conditions. Main hit ball initial conditions are ball initial velocity, launch angle, and back spin. The predicted flight distance is calculated by inputting the ball initial velocity, the launch angle, and the back spin to a three-dimensional ball trajectory simulation function (ball trajectory equation). The three-dimensional ball trajectory equation is created by a combination of actual measurement and simulation.

The ball initial velocity is calculated by inputting various information to a predetermined ball initial velocity predict function. Various information includes the mass of the golf club, the center of gravity depth, rightward/leftward moment of inertia, upward/downward moment of inertia, restitution coefficient, slip coefficient, head speed at impact, loft angle at impact, and attack angle at impact. The loft angle at impact is calculated based on the loft angle (original loft angle) of the golf club and the shaft lean angle at impact. The ball initial velocity predict function is created by a combination of actual measurement and simulation.

The launch angle is calculated by inputting the above-noted various information to a predetermined launch angle predict function. The launch angle predict function is created by a combination of actual measurement and simulation.

The back spin is calculated by inputting the above-noted various information to a predetermined back spin predict function. The back spin predict function is created by a combination of actual measurement and simulation.

Next, transition button 1508 is selected to make a transition to the shaft select screen (not shown). In the shaft select screen, the iron shaft recommended in iron shaft recommend screen 1350 shown in FIG. 17 is selected. When the iron shaft is selected, a grip select screen (not shown) appears in accordance with an instruction by the fitter. When a grip is selected in the grip select screen, an iron confirmation screen shown in FIG. 22 appears in accordance with an instruction by the fitter.

FIG. 22 is a diagram showing an example of the confirmation screen for the selected iron. Referring to FIG. 22, confirmation screen 1550 includes a region 1552 for displaying the measured parameters, a region 1554 for displaying the selected iron model, number, shaft, and grip, a button 1556 for going back to the previous screen, a transition button 1558 for making a transition to the utility select screen, a transition button 1560 for going back to the iron select screen, a transition button 1562 for making a transition to the wedge select screen, and a complete button 1564. When confirmation of the selected iron is finished, the fitter selects transition button 1562.

Figure 23:
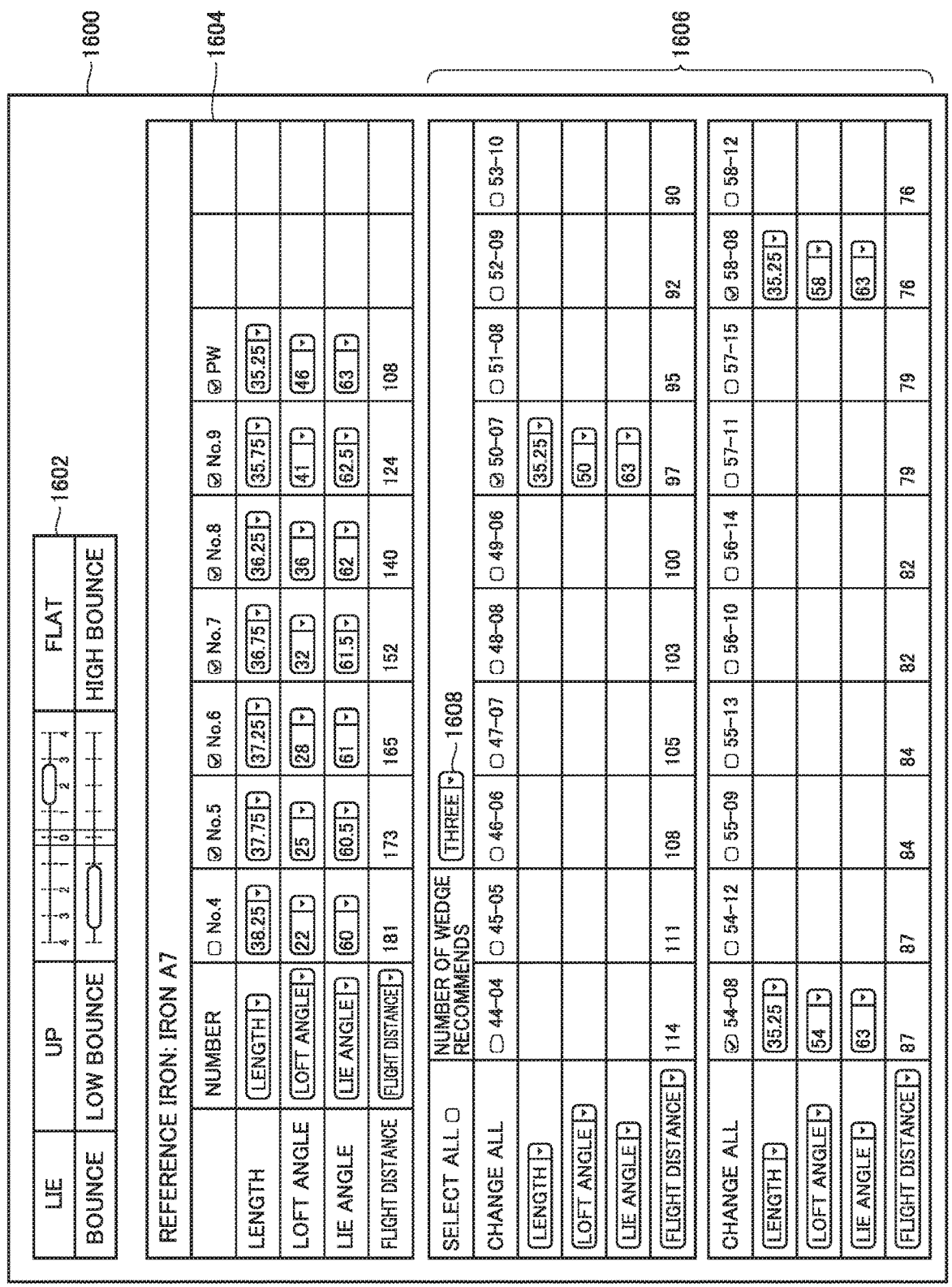
FIG. 23 is a diagram showing an example of a wedge head select screen.

FIG. 23 is a diagram showing an example of the wedge head select screen. Referring to FIG. 23, wedge head select screen 1600 includes a region 1602 for displaying spec information of the wedge recommended for the user, a region 1604 similar to region 1504 in FIG. 21, and a region 1606 for displaying information about the recommended wedge.

Region 1602 shows the lie and the bounce recommended for the user. In the example in FIG. 23, "flat" lie angle is recommended rather than "up", and "high bounce" bounce is recommended rather than "low bounce". The bounce is determined by the recommended loft angle. As the recommended loft angle is closer to 27 degrees, "low bounce" is recommended, and as the recommended loft angle is closer to 36 degrees, "high bounce" is recommended.

Region 1606 shows the specs of three recommended wedges (for example, length of shaft, loft angle, lie angle) and also shows the corresponding predicted flight distances. Region 1604 shows the predicted flight distance for each iron number. This allows the user to view the predicted flight distance for each iron number and the predicted flight distance for a wedge at the same time. That is, the user can select a wedge head by referring to the predicted flight distance of the selected iron number. The user also can change the number of recommended wedges to two by selecting an object 1608.

FIG. 24 is a diagram showing another example of the wedge head select screen. Referring to FIG. 24, the number of wedges "2" is selected in object 1608 so that two recommended wedge heads are displayed in region 1606.

Next, when the user selects a wedge head, the screen makes a transition to a wedge shaft and wedge grip select screen (not shown) in accordance with an instruction by the fitter. When a wedge shaft and a wedge grip are selected, a wedge confirmation screen appears. When selection of a wedge is finished, the screen makes a transition to the utility select screen in accordance with an instruction by the fitter.

FIG. 25 is a diagram showing an example of the utility head select screen. Referring to FIG. 25, utility head select screen 1650 includes a region 1652 for displaying spec information of a head recommended for the user, a region 1654 similar to region 1504 in FIG. 21, a region 1656 for displaying information about the recommended utility head, a button 1658 for going back to the previous screen, and a button 1660 for making a transition to a utility shaft select screen.

Region 1656 shows the specs (for example, length of shaft, loft angle, lie angle) for each utility number and also shows the corresponding predicted flight distance. Region 1654 shows the predicted flight distance for each iron number. This allows the user to view the predicted flight distance for each iron number and the predicted flight distance of a utility at the same time.

When the user selects a utility head, the screen makes a transition to a utility shaft and utility grip select screen (not shown) in accordance with an instruction by the fitter. When a utility shaft and a utility grip are selected, a utility confirmation screen appears. When selection of a utility is finished, a finalize screen appears in accordance with an instruction by the fitter. As described above, fitting of an iron, a wedge, and a utility is performed.

<Functional Configuration>

Figure 26:
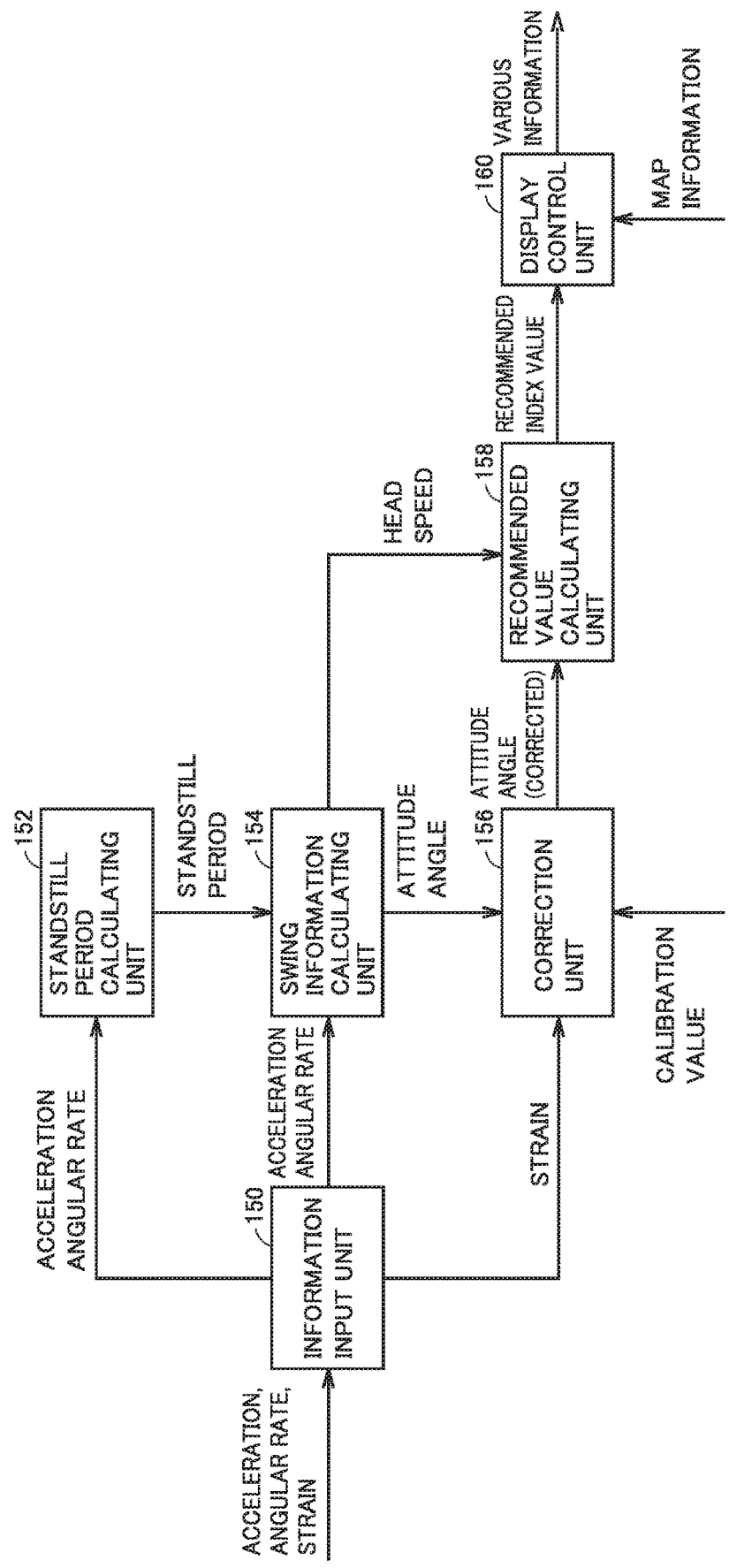
FIG. 26 is a functional block diagram of the swing analysis device.

FIG. 26 is a functional block diagram of swing analysis device 10. Referring to FIG. 26, swing analysis device 10 includes, as a main functional configuration, an information input unit 150, a standstill period calculating unit 152, a swing information calculating unit 154, a correction unit 156, a recommended value calculating unit 158, and a display control unit 160. Basically, these are implemented by processor 102 of swing analysis device 10 executing a program stored in memory 104 and giving an instruction to the components in swing analysis device 10. That is, processor 102 functions as a control unit to control the entire operation of swing analysis device 10. Part or whole of the functional configuration may be implemented by hardware.

Information input unit 150 accepts input of acceleration information, angular rate information, and strain information detected by sensor device 20 attached to golf club 50. Information input unit 150 also accepts input of "swing tempo", "kick angle", "toe down amount", and "release factor" calculated by sensor device 20. Typically, information input unit 150 receives these pieces of information transmitted from sensor device 20 through communication interface 120. However, information input unit 150 may accept input of these pieces of information through touch panel 106 (or button 108).

Standstill period calculating unit 152 calculates a standstill period in accordance with the (standstill detection method) above. Standstill period calculating unit 152 calculates time t1 when the combined angular rate W based on the angular rate information reaches the reference threshold Th. More specifically, standstill period calculating unit 152 calculates the combined acceleration AC and calculates the time when the amount of change per unit time of the combined acceleration AC reaches a threshold or more, as an impact time. Standstill period calculating unit 152 calculates time t1 when the combined angular rate W is less than the reference threshold Th, back to the time before the impact time by a predetermined amount of time.

Standstill period calculating unit 152 calculates period Tc from time t2 prior to time t1 by the amount of time Ta (for example, 0.5 second) to time t3 prior to time t1 by the amount of time Tb, as a standstill period during which the golfer stays still.

Swing information calculating unit 154 calculates the attitude information of golf club 50 in accordance with the (attitude calculation method) above. Specifically, swing information calculating unit 154 calculates the attitude angle at address of the user immediately before the start of the swing period, based on the acceleration information in standstill period Tc.

Swing information calculating unit 154 calculates the attitude angle from the start to the end (at impact) of the swing period. In particular, swing information calculating unit 154 calculates the lie angle Lc, the shaft lean angle SLc, the attack angle ATc, the face angle FAc, and the swing path SWc, as the attitude angle of the golf club at impact.

In another aspect, swing information calculating unit 154 further calculates the head speed Vhs at impact, based on the acceleration information and the angular rate information. When the user swings the golf club multiple times, swing information calculating unit 154 further calculates the standard deviation Vsd of the head speed Vhs at impact.

Correction unit 156 corrects the attitude information of golf club 50 at impact calculated by swing information calculating unit 154, based on the strain information of the shaft of golf club 50. Specifically, correction unit 156 corrects the lie angle Lc at impact calculated by swing information calculating unit 154, based on the strain amount Dy in the toe down direction Ey at impact. That is, correction unit 156 calculates the lie angle La at impact using Equation (10). Equation (10) is a regression equation obtained by performing regression analysis where the strain amount Dy and the lie angle Lc at impact are explanatory variables and the actually measured value of the lie angle at impact is an object variable.

Correction unit 156 corrects the shaft lean angle at impact SLc calculated by swing information calculating unit 154, based on the strain amount Dx in the hit ball direction Ex at impact. That is, correction unit 156 calculates the shaft lean angle at impact SLa using Equation (11). Equation (11) is a regression equation obtained by performing regression analysis where the strain amount Dx, the shaft lean angle SLc at impact, the face angle FAc, and the swing path SWc are explanatory variables and the actually measured value of the shaft lean angle at impact is an object variable.

In another aspect, correction unit 156 further corrects the calculated lie angle La and shaft lean angle SLa at impact, based on the calibration values stored in memory 104. Specifically, correction unit 156 corrects the lie angle La at impact to the lie angle Lf using the calibration value H_LIE. Correction unit 156 corrects the shaft lean angle SLa at impact to the shaft lean angle SLf, using the calibration value H_SL.

The calibration value H_LIE is the difference between a predetermined angle and the lie angle calculated by swing information calculating unit 154 when the lie angle of golf club 50 is set to the predetermined angle in a state in which shaft 52 of golf club 50 is fixed by a jig placed on a plane parallel to the ground. The calibration value H_SL is the shaft lean angle calculated by swing information calculating unit 154 when the lie angle of golf club 50 is set to a predetermined angle.

Recommended value calculating unit 158 calculates the right/left index value (corresponding to the right/left recommended value Krl) recommended for the user, using the relative face angle Frf at impact, the head speed Vhs at impact, and the standard deviation Vsd of the head speed Vhs. Recommended value calculating unit 158 calculates the up/down index value (corresponding to the up/down recommended value Kud) recommended for the user, using the attack angle ATf at impact, the shaft lean angle SLf at impact, the head speed Vhs at impact, and the standard deviation Vsd.

Display control unit 160 displays a presentation screen (for example, a screen including map 30 shown in FIG. 19) on display 110 to present a golf club suitable for the user from among a plurality of golf clubs prepared in advance.

Specifically, for each of a plurality of golf clubs prepared in advance, display control unit 160 displays information (for example, points A1 to A8) based on the right/left index value and the up/down index value of the golf club on the presentation screen. For each of a plurality of golf clubs prepared in advance, display control unit 160 displays information (for example, points A1 to A8) based on the right/left index value and the up/down index value of the golf club, on the presentation screen. Display control unit 160 further displays information (for example, circle region 1441) based on the right/left recommended value Krl and the up/down recommended value Kud calculated by the recommended value calculating unit 158, on the presentation screen.

Display control unit 160 further displays information (for example, point H) based on the attack angle ATf and the relative face angle Frf on the presentation screen. Display control unit 160 displays a screen (for example, utility head select screen 1650 in FIG. 25) including the predicted flight distance of the golf club 50 and the predicted flight distance of a golf club of a type (for example, utility type) different from the type of golf club 50 (for example, iron type) on display 110. The screen also includes the predicted flight distance of a number (for example, 5) different from the number of golf club 50 (for example, 7). Display control unit 160 further displays a variety of screens described above on display 110.

<Appearance of Sensor Device 20>

Figure 27:
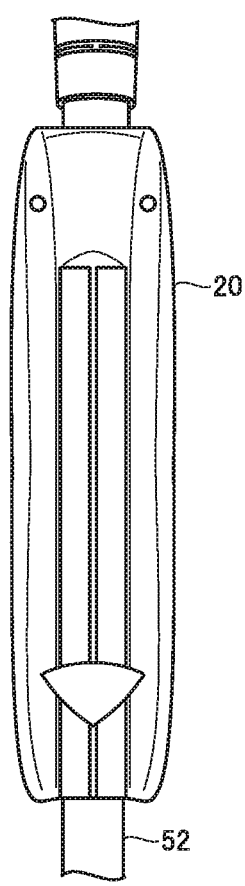
FIG. 27 is a diagram showing the appearance of the sensor device.

FIG. 27 is a diagram showing the appearance of sensor device 20. Specifically, FIG. 27 is an enlarged view of sensor device 20 in FIG. 1.

<Other Embodiments>

(1) In the foregoing embodiment, the parameters for calculating the right/left recommended value are the relative face angle at impact, the head speed at impact, and the standard deviation of the head speed. However, embodiments are not limited to this configuration. The parameter may be only the relative face angle. Alternatively, the parameters may include either the relative face angle or the head speed and the standard deviation.

(2) In the foregoing embodiment, the parameters for calculating the up/down recommended value are the attack angle at impact, the shaft lean angle, the head speed at impact, and the standard deviation. However, embodiments are not limited to this configuration. The parameters may be only the attack angle and the shaft lean angle. Alternatively, the parameters may include either the attack angle and the shaft lean angle or the head speed and the standard deviation.

(3) In the foregoing embodiment, the right/left recommended value and the up/down recommended value are calculated based on the lie angle, the shaft lean angle, and the like calculated by correction unit 156. However, embodiments are not limited to this configuration. For example, the correction process by correction unit 156 may not be performed when it is desired to perform a simpler swing analysis for fitting, for example, for alleviating processing loads.

(4) In the foregoing embodiment, the regression equation (11) is used to calculate the corrected value SLa of the shaft lean angle. However, embodiments are not limited to this configuration. Specifically, the corrected value SLa of the shaft lean angle may be calculated using the regression equation (20) below obtained by performing multiple regression analysis where the shaft lean angle SLc at impact and the strain amount Dx in the hit ball direction Ex at impact are explanatory variables and the actually measured value of the shaft lean angle at impact is an object variable. Here, g0, g1, g2 are multiple regression coefficients.

$$SLa = g1 \times (Dx) + g2 \times SLc + g0 \quad (20)$$

As the determination coefficient $R^2$ of the multiple regression equation shown in Equation (20) is 0.3964, a high determination coefficient is obtained and the shaft lean angle can be calculated accurately.

(5) A program may be provided which causes a computer to function to perform the control as described above. Such a program may be recorded on a non-transitory computer-readable storage medium accompanying the computer, such as a flexible disk, a CD-ROM (Compact Disk Read Only Memory), a ROM, a RAM, and a memory card and provided as a program product. Alternatively, the program may be recorded on a storage medium such as a hard disk contained in the computer. The program may be downloaded through a network.

The program may be configured such that necessary modules of program modules provided as part of an operating system (OS) of the computer are invoked at a predetermined timing to execute a process. In this case, the program itself does not include the modules, and the process is executed in cooperation with the OS. Such a program that does not include the modules may be included in the program according to the present embodiment.

The program according to the present embodiment may be built in part of another program and provided. Also in this case, the program itself does not include modules included in the other program, and the process is executed in cooperation with the other program. Such a program built in another program may also be embraced in the program according to the present embodiment.

The configuration illustrated as an embodiment as described above is an example of the configuration of the present invention and may be combined with another known technique or may be changed, for example, partially omitted, without departing from the spirit of the present invention.

<Effects of Embodiments>

The present embodiment can accurately calculate the attitude angle at impact by considering the strain of the shaft at impact and therefore can improve the swing analysis accuracy. By improving the swing analysis accuracy, it is possible to recommend the user for a proper golf club.

According to the present embodiment, a map for selecting a golf club suitable for the user appears on the display to allow the user to grasp which golf club is suitable for him/her.

The embodiments disclosed here should be understood as being illustrative rather than being limitative in all respects. The scope of the present invention is shown not in the foregoing description but in the claims, and it is intended that all modifications that come within the meaning and range of equivalence to the claims are embraced here.

REFERENCE SIGNS LIST 10 swing analysis device, 20 sensor device, 30 map, 50 golf club, 52 shaft, 102, 202 processor, 104, 204 memory, 106 touch panel, 108 button, 110 display, 112 wireless communication unit, 113 communication antenna, 114 memory interface, 115 storage medium, 116 speaker, 118 microphone, 120 communication interface, 150 information input unit, 152 standstill period calculating unit, 154 swing information calculating unit, 156 correction unit, 158 recommended value calculating unit, 160 display control unit, 206 acceleration sensor, 208 angular rate sensor, 210 strain sensor, 214 storage battery, 220, 221 strain gauge, 1000 swing analysis system.

The invention claimed is:

1. A swing analysis device for analyzing a swing of a user of a golf club, comprising:
an information input unit configured to accept input of acceleration information, angular rate information, and strain information of a shaft of the golf club, detected by a sensor attached to the shaft;
an attitude calculating unit configured to calculate attitude information of the golf club in a swing period, based on the acceleration information and the angular rate information;
a correction unit configured to correct attitude information of the golf club at impact, based on the strain information of the shaft; and
a display control unit configured to display the attitude information of the golf club corrected by the correction unit on a display.

2. The swing analysis device according to claim 1, wherein
the attitude information includes a lie angle indicating an angle of the shaft of the golf club relative to ground,
the strain information includes a strain amount in a toe down direction of the shaft, and
the correction unit corrects a lie angle at the impact calculated by the attitude calculating unit, based on a strain amount in the toe down direction at the impact.

3. The swing analysis device according to claim 2, wherein the correction unit corrects the calculated lie angle at the impact using a first regression equation obtained by performing regression analysis where the strain amount in the toe down direction at the impact and the calculated lie angle at the impact are explanatory variables and an actually measured value of a lie angle at the impact is an object variable.

4. The swing analysis device according to claim 1, wherein
the attitude information further includes a shaft lean angle indicating an angle of the shaft relative to a virtual plane normal to ground,
the strain information further includes a strain amount in a hit ball direction of the shaft, and
the correction unit corrects a shaft lean angle at the impact calculated by the attitude calculating unit, based on a strain amount in the hit ball direction at the impact.

5. The swing analysis device according to claim 4, wherein
the correction unit corrects the calculated shaft lean angle at the impact, using a second regression equation obtained by performing regression analysis where the strain amount in the hit ball direction at the impact and the calculated shaft lean angle at the impact are explanatory variables and an actually measured value of a shaft lean angle at the impact is an object variable.

6. The swing analysis device according to claim 1, further comprising a standstill period calculating unit configured to calculate a first time when a combined angular rate based on the angular rate information reaches a reference threshold and calculate a period from a second time prior to the first time by a first amount of time to a third time prior to the first time by a second amount of time, as a standstill period during which the user stays still,
wherein the attitude calculating unit calculates attitude information at address of the user immediately before start of the swing period, based on the acceleration information in the standstill period.

7. The swing analysis device according to claim 1, further comprising an information storage unit configured to store a difference between a predetermined angle and a lie angle calculated by the attitude calculating unit when the lie angle of the golf club is set to the predetermined angle in a state in which the shaft of the golf club is fixed by a jig placed on a plane parallel to ground, as a calibration value of the lie angle, and store a shaft lean angle calculated by the attitude calculating unit when the lie angle is set to the predetermined angle, as a calibration value of the shaft lean angle.

8. The swing analysis device according to claim 1, wherein the display control unit is configured to display a presentation screen on the display to present a golf club suitable for the user from among a plurality of golf clubs prepared in advance, wherein for each of the golf clubs prepared in advance, the display control unit displays first information based on a first index value serving as an index of flight characteristics in a right and left direction of a hit ball in the golf club and a second index value serving as an index of flight characteristics in an up and down direction of a hit ball in the golf club, on the presentation screen, the attitude information further includes an attack angle indicating an angle of a direction of a swing trajectory relative to ground at impact and a relative face angle obtained by subtracting an angle of approach from a face angle, the face angle indicating an angle of a face plane of the golf club relative to a virtual plane orthogonal to a target line direction, the angle of approach indicating an angle formed with the target line direction relative to a direction of the swing trajectory, the swing analysis device further comprises a recommended value calculating unit configured to calculate a first index value recommended for the user based on a first parameter including the relative face angle and calculate a second index value recommended for the user based on a second parameter including the attack angle, the display control unit further displays second information based on the first index value recommended for the user and the second index value recommended for the user, calculated by the recommended value calculating unit, on the presentation screen.

9. The swing analysis device according to claim 8, wherein the display control unit further displays third information indicating the attack angle and the relative face angle calculated by the attitude calculating unit, on the presentation screen.

10. The swing analysis device according to claim 8, further comprising a head speed calculating unit configured to calculate a head speed of the golf club in a swing period, based on the acceleration information and the angular rate information, wherein the first parameter and the second parameter further include a head speed at the impact.

11. The swing analysis device according to claim 10, wherein when the user swings the golf club multiple times, the head speed calculating unit further calculates a standard deviation of the head speed at the impact multiple times, and the first parameter and the second parameter further include the standard deviation.

12. The swing analysis device according to claim 8, wherein the display control unit displays a screen including a predicted flight distance of the golf club and a predicted flight distance of a golf club of a number different from the number of the golf club, on the display.

13. The swing analysis device according to claim 12, wherein the display control unit further displays a predicted flight distance of another golf club of a type different from the type of the golf club, and the type includes at least two of iron type, wedge type, and utility type.

14. A swing analysis method for analyzing a swing of a user of a golf club, comprising the steps of:

accepting input of acceleration information, angular rate information and strain information of a shaft of the golf club, detected by a sensor attached to the shaft;

calculating attitude information of the golf club in a swing period, based on the acceleration information and the angular rate information;

correcting attitude information of the golf club at impact, based on the strain information of the shaft; and displaying the corrected attitude information of the golf club.

15. A swing analysis system for analyzing a swing of a user of a golf club, comprising:

a sensor device attached to a shaft of the golf club; and a swing analysis device for analyzing a swing of the user based on information detected by the sensor device, the swing analysis device comprising an information input unit configured to accept input of acceleration information, angular rate information, and strain information of the shaft, detected by the sensor device, an attitude calculating unit configured to calculate attitude information of the golf club in a swing period, based on the acceleration information and the angular rate information, a correction unit configured to correct attitude information of the golf club at impact, based on the strain information of the shaft, and a display control unit configured to display the attitude information of the golf club corrected by the correction unit on a display.

\* \* \* \* \*